United States Patent
Cook, II et al.

(10) Patent No.: US 10,174,052 B2
(45) Date of Patent: Jan. 8, 2019

(54) QUINUCLIDINE COMPOUNDS AS α-7 NICOTINIC ACETYLCHOLINE RECEPTOR LIGANDS

(71) Applicant: BRISTOL-MYERS SQUIBB COMPANY, Princeton, NJ (US)

(72) Inventors: James H. Cook, II, East Hampton, CT (US); F. Christopher Zusi, Hamden, CT (US); Matthew D. Hill, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/523,416

(22) PCT Filed: Nov. 3, 2015

(86) PCT No.: PCT/US2015/058720
§ 371 (c)(1),
(2) Date: May 1, 2017

(87) PCT Pub. No.: WO2016/073407
PCT Pub. Date: May 12, 2016

(65) Prior Publication Data
US 2017/0305929 A1  Oct. 26, 2017

Related U.S. Application Data

(60) Provisional application No. 62/074,815, filed on Nov. 4, 2014.

(51) Int. Cl.
*C07D 498/22* (2006.01)
*A61K 31/439* (2006.01)
*C07D 498/10* (2006.01)

(52) U.S. Cl.
CPC .......... *C07D 498/22* (2013.01); *A61K 31/439* (2013.01); *C07D 498/10* (2013.01)

(58) Field of Classification Search
CPC ..................................................... C07D 498/22
USPC ......................................................... 514/278
See application file for complete search history.

(56) References Cited

U.S. PATENT DOCUMENTS

| 7,863,291 B2 | 1/2011 | Cook, II et al. |
| 8,309,577 B2 | 11/2012 | Cook, II et al. |
| 9,458,179 B2 | 10/2016 | Hill et al. |

FOREIGN PATENT DOCUMENTS

| WO | WO 03/087102 A1 | 10/2003 | |
| WO | WO-2011053292 A1 * | 5/2011 | ........... C07D 498/20 |
| WO | WO-2013177024 A1 * | 11/2013 | ........... C07D 453/02 |

OTHER PUBLICATIONS

Pohanka, M., "Alpha7 Nicotinic Acetylcholine Receptor Is a Target in Pharmacology and Toxicology," International Journal of Molecular Sciences, 13, pp. 2219-2238 (2012).

* cited by examiner

*Primary Examiner* — Rita J Desai
(74) *Attorney, Agent, or Firm* — Elliott Korsen

(57) ABSTRACT

There are disclosed a series of quinuclidines having the Formula (I), which bind to the nicotinic α7 receptor and may be useful for the treatment of disorders of the central nervous system.

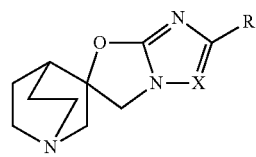

(I)

13 Claims, No Drawings

QUINUCLIDINE COMPOUNDS AS α-7 NICOTINIC ACETYLCHOLINE RECEPTOR LIGANDS

CROSS-REFERENCE TO RELATED APPLICATIONS

This application claims the benefit of U.S. Provisional Application No. 62/074,815, filed Nov. 4, 2014, the disclosure of which is incorporated herein by reference in its entirety.

FIELD OF THE DISCLOSURE

This patent application provides novel substituted amino oxazolidine quinuclidine compounds having drug and bio-affecting properties, their pharmaceutical compositions and method of use. In particular, the disclosure is concerned with a series of substituted fused imidazo[2,1-b]oxazolidine or oxazolo[3,2-b][1,2,4]triazole quinuclidines which bind to the nicotinic α7 receptor and are useful for the treatment of various disorders of the central nervous system. More particularly, the present disclosure relates to the treatment of affective disorders and neurodegenerative disorders.

BACKGROUND OF THE INVENTION

The disclosure generally relates to compounds of formulas I and II, including their salts, as well as compositions and methods of using the compounds. The compounds are ligands, agonists and partial agonists for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood; however most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs pre-synaptically. The localization of α7 nAChRs in areas involved with learning and memory has led to studies using both knockout mice and pharmacological manipulation. It is involved in sensory gating, memory, and neuronal plasticity. Alpha7 agonists have been shown to increase the release of neurotransmitters in rodents, including dopamine, serotonin, glutamate and GABA. Compounds which selectively bind to the α7 receptor, such as α7 agonists and partial agonists, have been shown to improve learning and memory functions in normal and aged animals, reverse scopolamine-induced memory deficits, reverse deficits in cognition induced by NMDA antagonists, reverse pharmacologically-induced gating deficits, e.g. amphetamine induced gating disruption, and to possess some anxiolytic properties. The α7 agonists of the present invention are expected to be useful in the treatment of schizophrenia and cognitive disorders associated with schizophrenia.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living, and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks. This clinical data is consistent with pre-clinical data showing α7 agonists and partial agonists improve learning and memory functions in normal and aged animals and reverse scopolamine-induced memory deficits. Thus, the compounds of the present invention may be useful in the treatment and prevention of Alzheimer's disease. The amyloid peptide Aβ42 has been shown to bind to the α7 nicotinic receptor (Wang et al., J. Biol. Chem., 2000, 275:5626-5632; J. Neurochem. 2000, 75:1155-1161). This association may facilitate the aggregation of Aβ42, believed to be important in the toxic effects of Aβ42, and may also cause dysregulation of signaling through α7 nicotinic receptors. Deletion of the α7 receptor gene improves cognitive deficits and synaptic pathology in a mouse model of Alzheimer's disease (Dziewczapolski et al., J. Neuroscience, 2009, pp 8805-8815). The compounds of the present invention may disrupt the interaction of Aβ42 and α7 receptors. Alpha7 receptors may also mediate inflammatory processes in neurodegenerative conditions, such as Alzheimer's disease (Conejero-Goldberg et al., Neurosci. and Biobehav. Rev., 2008, 32, pp 693-706). The α7 agonists and partial agonists of the present invention may be useful in reducing inflammation in neurodegenerative diseases and disorders, such as Alzheimer's disease.

The α7 receptor has also been shown to be involved in the reduction of inflammation via the vagus nerve. In addition, the α7 receptor is expressed in synoviocytes from RA and OA patients, and α7 agonists have been shown to inhibit the proinflammatory cascade that occurs in the rheumatoid joint (Waldberger et al., Arthritis and Rheumatism, Vol 58, pp 3439-3449). Thus, the compounds of the present invention may be useful in the treatment of inflammatory conditions, such as rheumatoid arthritis and osteoarthritis.

Nicotinic receptors containing the α7 subunit are present on mucosal mast cells known to be involved in gastrointestinal hypersensitivity (Kageyama-Yahara et al., Biochem and Biophys. Research Commun., 2008, v. 377, pp 321-325). The α7 agonist GTS-21 inhibits the antigen-induced degranulation of mucosal mast cells, suggesting that α7 agonists may be useful in the treatment of hypersensitive bowel conditions, such as ulcerative colitis.

In a recent report (Marrero et al., J. Pharmacol. Exp. Ther. (2010) 332: 173-80), an α7 agonist was shown to decrease weight gain and food intake and reduce the elevated plasma levels of triglycerides, glucose, glycated hemoglobin and TNFα in a mouse model of type II diabetes (db/db mice which are deficit in leptin receptors). The α7 agonists and partial agonists of the present invention may be useful in the treatment of diabetes.

The following references provide general reviews of the nicotinic receptor system and α7 receptors and ligands: Picciotto and Zoli, J. Neurobio. (2002) 53:641-655; Brening, et al, Ann. Reports in Med. Chem. (2005) 40:3-16; Dani and Bertrand, Ann. Rev. Pharm. Tox. (2007) 47:699-729; Olincy and Stevens, Biochem. Pharmacol. (2007) 74:1192-1201; Broad, et al, Drugs Future (2007) 32 (2):161-70; de Jonge and Ulloa, Brit. J. Pharmacol. (2007) 151:915-929; Romanelli, et al, ChemMedChem (2007) 2(6):746-767; Lightfoot et al., Progress in Medicinal Chemistry (2008), v 46, pp 131-171; Concotta et al., Current Opinion in Investigational Drugs (2008), v 9, pp 47-56; Leiser et al., Pharmacol. and Therapeutics (2009), doi:10:1016/j.pharmthera.2009.03.009).

Ligands for the nicotinic α7 receptor have been disclosed in the references above, and also in US patent application publication U.S. 2007004715, WO 2011-053292, U.S. Pat. No. 7,863,291, WO 2008/000469, WO 2003/092580, WO 2004/000,469, EP 337,547, EP 452,101, and C. J. Swain, et al., J. Med. Chem., (1992) 35:1019-1031.

The invention provides technical advantages; for example, the compounds are novel and are ligands for the nicotinic α7 receptor and may be useful for the treatment of various disorders of the central nervous system, especially affective and neurodegenerative disorders. Additionally, the compounds provide advantages for pharmaceutical uses, for example, with regard to one or more of their mechanism of action, binding, inhibition efficacy, target selectivity, solubility, safety profiles, or bioavailability.

SUMMARY OF THE INVENTION

There are disclosed a series of quinuclidines having the Formula I

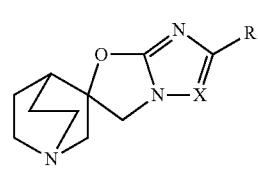

including fused imidazo[2,1-b]oxazolidine quinuclidines of Formula II

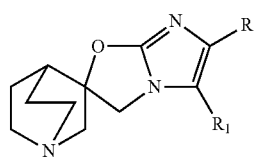

and oxazolo[3,2-b][1,2,4]triazole quinuclidines of Formula III

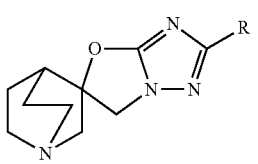

or stereoisomers; or pharmaceutically acceptable salts thereof. The compounds are effective ligands for the nicotinic α7 receptor and are useful for the treatment of disorders of the CNS involving the nicotinic cholinergic system. The pharmacologic action of these compounds makes them useful for treating affective disorders such as schizophrenia, anxiety, mania, depression, as well as neurodegenerative disorders such as Alzheimer's disease (AD), Parkinson's disease, Huntington's disease and cognitive disorders. Therapy utilizing administration of these compounds or a pharmaceutical composition containing a therapeutically effective amount of at least one of these compounds to patients suffering from disorders of the nicotinic cholinergic system is thereby enabled.

DETAILED DESCRIPTION OF THE INVENTION

The invention encompasses compounds of formulas I and II, including pharmaceutically acceptable salts, and compositions and methods of treatment using these compounds. The compounds may be useful for the treatment of various disorders of the central nervous system.

One aspect of the invention is a compound of formula I, or a stereoisomer thereof,

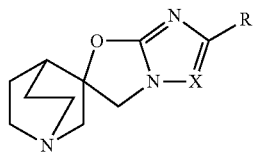

wherein
X is —N— or C—$R_1$;
R is H, $C_1$-$C_6$ alkyl, halo, halo $C_1$-$C_6$ alkyl, phenyl, substituted phenyl;
$R_1$ is H, $C_1$-$C_6$ alkyl, halo, halo $C_1$-$C_6$ alkyl, phenyl, substituted phenyl, or
R and $R_1$ can be together to form an aryl or heteroaryl ring, which may be further substituted by 1-3 substituents independently selected from $C_1$-$C_6$ alkyl, halo, halo $C_1$-$C_6$ alkyl, alkoxy, trifluoromethyl, phenyl, substituted phenyl or pyridyl or a pharmaceutically acceptable salt thereof.

Another aspect of the invention is a compound of formula II, or a stereoisomer thereof,

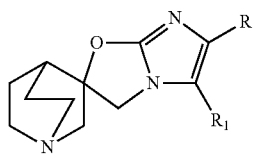

wherein:
R and $R_1$ are independently H, $C_1$-$C_6$ alkyl, halo, halo $C_1$-$C_6$ alkyl, phenyl, substituted phenyl, or together form an aryl or heteroaryl ring, which may be further substituted by 1-3 substituents independently selected from $C_1$-$C_6$ alkyl, halo, halo $C_1$-$C_6$ alkyl, alkoxy, trifluoromethyl, phenyl, substituted phenyl or pyridyl.

Another aspect of the invention is a compound of formula III or a stereoisomer thereof

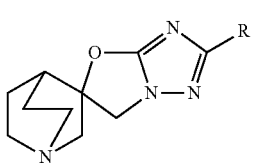

wherein R is H, $C_1$-$C_6$ alkyl, halo, halo $C_1$-$C_6$ alkyl, phenyl, or substituted phenyl; or a pharmaceutically acceptable salt thereof.

In another aspect of the invention there is disclosed a compound of formula II wherein
R and $R_1$ are independently H, halo, $C_1$-$C_3$ alkyl or phenyl.

In another aspect of the invention there is disclosed a compound of formula II wherein
R and $R_1$ are independently H, Br, Cl, $CH_3$ or phenyl.

In another aspect of the invention there is disclosed a compound of formula II wherein
R and $R_1$ are taken together to form an aryl or heteroaryl ring, which may be further substituted by 1-3 substituents independently selected from $C_1$-$C_6$ alkyl, halo, halo $C_1$-$C_6$ alkyl, alkoxy, $CF_3$, phenyl, substituted phenyl or pyridyl.

In another aspect of the invention there is disclosed a compound of formula II wherein
R and $R_1$ are taken together to form a phenyl ring which may be further substituted by 1-3 substituents independently selected from $C_1$-$C_6$ alkyl, halo, halo $C_1$-$C_6$ alkyl, $C_1$-$C_6$ alkoxy, $CF_3$, phenyl, substituted phenyl or pyridyl.

In another aspect of the invention there is disclosed a compound of formula II wherein
R and $R_1$ are taken together to form a phenyl ring which may be further substituted by 1-3 substituents independently selected from $CH_3$, Cl, Br, $OCH_3$, $CF_3$, phenyl, phenyl substituted with $CH_3$ or phenyl substituted with pyridyl.

In another aspect of the invention there is disclosed a compound of formula II wherein
R and $R_1$ are taken together to form a pyridyl ring which may be further substituted by 1-3 substituents independently selected from $C_1$-$C_6$ alkyl, halo, halo $C_1$-$C_6$ alkyl, alkoxy, $CF_3$, phenyl, substituted phenyl or pyridyl.

In another aspect of the invention there is disclosed a compound of formula II wherein
R and $R_1$ are taken together to form a pyridyl ring which may be further substituted by 1-2 substituents independently selected from $C_1$-$C_3$ alkyl or halo.

In another aspect of the invention there is disclosed a compound of formula II wherein
R and $R_1$ are taken together to form a pyridyl ring which may be further substituted by 1-2 substituents independently selected from Br, Cl or $CH_3$.

In another aspect of the invention there is disclosed a compound of formula III wherein
R is H, halo or phenyl.

In another aspect of the invention there is disclosed a compound of formula III wherein
R is H, Br, Cl or phenyl.

In another aspect of the invention, there are disclosed the following compounds of the invention
(R)-5,6-dibromo-3H-1'-azaspiro[imidazo[2,1-b]oxazole-2,3'-bicyclo[2.2.2]octane];
(S)-5,6-dibromo-3H-1'-azaspiro[imidazo[2,1-b]oxazole-2,3'-bicyclo[2.2.2]octane];
(R)-5,6-dichloro-3H-1'-azaspiro[imidazo[2,1-b]oxazole-2,3'-bicyclo[2.2.2]octane];
(S)-5,6-dichloro-3H-1'-azaspiro[imidazo[2,1-b]oxazole-2,3'-bicyclo[2.2.2]octane];
5-bromo-6-methyl-3H-1'-azaspiro[imidazo[2,1-b]oxazole-2,3'-bicyclo[2.2.2]octane];
6-bromo-5-methyl-3H-1'-azaspiro[imidazo[2,1-b]oxazole-2,3'-bicyclo[2.2.2]octane];
(R)-3H-1'-azaspiro[benzo[4,5]imidazo[2,1-b]oxazole-2,3'-bicyclo[2.2.2]octane];
(S)-3H-1'-azaspiro[benzo[4,5]imidazo[2,1-b]oxazole-2,3'-bicyclo[2.2.2]octane];
(R)-6,7-dimethyl-3H-1'-azaspiro[benzo[4,5]imidazo[2,1-b]oxazole-2,3'-bicyclo[2.2.2]octane];
(S)-6,7-dimethyl-3H-1'-azaspiro[benzo[4,5]imidazo[2,1-b]oxazole-2,3'-bicyclo[2.2.2]octane];
(R)-7-methoxy-3H-1'-azaspiro[benzo[4,5]imidazo[2,1-b]oxazole-2,3'-bicyclo[2.2.2]octane];
(S)-7-methoxy-3H-1'-azaspiro[benzo[4,5]imidazo[2,1-b]oxazole-2,3'-bicyclo[2.2.2]octane];
(R)-6-methoxy-3H-1'-azaspiro[benzo[4,5]imidazo[2,1-b]oxazole-2,3'-bicyclo[2.2.2]octane];
(S)-6-methoxy-3H-1'-azaspiro[benzo[4,5]imidazo[2,1-b]oxazole-2,3'-bicyclo[2.2.2]octane];
(R)-7-methyl-3H-1'-azaspiro[benzo[4,5]imidazo[2,1-b]oxazole-2,3'-bicyclo[2.2.2]octane];
(S)-7-methyl-3H-1'-azaspiro[benzo[4,5]imidazo[2,1-b]oxazole-2,3'-bicyclo[2.2.2]octane];
(R)-6-methyl-3H-1'-azaspiro[benzo[4,5]imidazo[2,1-b]oxazole-2,3'-bicyclo[2.2.2]octane];
(S)-6-methyl-3H-1'-azaspiro[benzo[4,5]imidazo[2,1-b]oxazole-2,3'-bicyclo[2.2.2]octane];
(R)-7-(trifluoromethyl)-3H-1'-azaspiro[benzo[4,5]imidazo[2,1-b]oxazole-2,3'-bicyclo[2.2.2]octane];
(S)-7-(trifluoromethyl)-3H-1'-azaspiro[benzo[4,5]imidazo[2,1-b]oxazole-2,3'-bicyclo[2.2.2]octane];
(R)-6-(trifluromethyl)-3H-1'-azaspiro[benzo[4,5]imidazo[2,1-b]oxazole-2,3'-bicyclo[2.2.2]octane];
(S)-6-(trifluoromethyl)-3H-1'-azaspiro[benzo[4,5]imidazo[2,1-b]oxazole-2,3'-bicyclo[2.2.2]octane];
(R)-8-chloro-3H-1'-azaspiro[benzo[4,5]imidazo[2,1-b]oxazole-2,3'-bicyclo[2.2.2]octane];
(S)-8-chloro-3H-1'-azaspiro[benzo[4,5]imidazo[2,1-b]oxazole-2,3'-bicyclo[2.2.2]octane];
(R)-5-chloro-3H-1'-azaspiro[benzo[4,5]imidazo[2,1-b]oxazole-2,3'-bicyclo[2.2.2]octane],
(S)-5-chloro-3H-1'-azaspiro[benzo[4,5]imidazo[2,1-b]oxazole-2,3'-bicyclo[2.2.2]octane];
(R)-8-methyl-3H-1'-azaspiro[benzo[4,5]imidazo[2,1-b]oxazole-2,3'-bicyclo[2.2.2]octane];
(S)-8-methyl-3H-1'-azaspiro[benzo[4,5]imidazo[2,1-b]oxazole-2,3'-bicyclo[2.2.2]octane];
(R)-8-(trifluoromethyl)-3H-1'-azaspiro[benzo[4,5]imidazo[2,1-b]oxazole-2,3'-bicyclo[2.2.2]octane];
(S)-8-(trifluoromethyl)1-3H-1'-azaspiro[benzo[4,5]imidazo[2,1-b]oxazole-2,3'-bicyclo[2.2.2]octane];
(R)-8-(4-methoxyphenyl))-3H-1'-azaspiro[benzo[4,5]imidazo[2,1-b]oxazole-2,3'-bicyclo[2.2.2]octane];
(S)-8-(4-methoxyphenyl))-3H-1'-azaspiro[benzo[4,5]imidazo[2,1-b]oxazole-2,3'-bicyclo[2.2.2]octane];
(R)-7-(pyridin-3-yl)-3H-1'-azaspiro[benzo[4,5]imidazo[2,1-b]oxazole-2,3'-bicyclo[2.2.2]octane];
(S)-7-(pyridin-3-yl)-3H-1'-azaspiro[benzo[4,5]imidazo[2,1-b]oxazole-2,3'-bicyclo[2.2.2]octane];
(R)-2-phenyl-6H-1'-azaspiro[oxazolo[3,2-b][1,2,4]triazole-5,3'-bicyclo[2.2.2]octane];
(S)-2-phenyl-6H-1'-azaspiro[oxazolo[3,2-b][1,2,4]triazole-5,3'-bicyclo[2.2.2]octane];
2-bromo-6H-1'-azaspiro[oxazolo[3,2-b][1,2,4]triazole-5,3'-bicyclo[2.2.2]octane];
2-chloro-6H-1'-azaspiro[oxazolo[3,2-b][1,2,4]triazole-5,3'-bicyclo[2.2.2]octane];
6H-1'-azaspiro[oxazolo[3,2-b][1,2,4]triazole-5,3'-bicyclo[2.2.2]octane];
7-bromo-6-methyl-3H-1'-azaspiro[oxazolo[2',3':2,3]imidazo[4,5-b]pyridine-2,3'-bicyclo[2.2.2]octane];
7-bromo-3H-1'-azaspiro[oxazolo[2',3':2,3]imidazo[4,5-b]pyridine-2,3'-bicyclo[2.2.2]octane];
7-chloro-3H-1'-azaspiro[oxazolo[2',3':2,3]imidazo[4,5-b]pyridine-2,3'-bicyclo[2.2.2]octane];
(R)-6-phenyl-3H-1'-azaspiro[imidazo[2,1-b]oxazole-2,3'-bicyclo[2.2.2]octane]; and
(S)-6-phenyl-3H-1'-azaspiro[imidazo[2,1-b]oxazole-2,3'-bicyclo[2.2.2]octane]
or a pharmaceutically acceptable salt or stereoisomer thereof.

In a further aspect of the invention, there are disclosed the following compounds of the invention
(R)-7-methoxy-3H-1'-azaspiro[benzo[4,5]imidazo[2,1-b]oxazole-2,3'-bicyclo[2.2.2]octane];
(R)-7-methyl-3H-1'-azaspiro[benzo[4,5]imidazo[2,1-b]oxazole-2,3'-bicyclo[2.2.2]octane];
R)-7-(trifluoromethyl)-3H-1'-azaspiro[benzo[4,5]imidazo[2,1-b]oxazole-2,3'-bicyclo[2.2.2]octane];
(R)-8-methyl-3H-1'-azaspiro[benzo[4,5]imidazo[2,1-b]oxazole-2,3'-bicyclo[2.2.2]octane];
(R)-2-phenyl-6H-1'-azaspiro[oxazolo[3,2-b][1,2,4]triazole-5,3'-bicyclo[2.2.2]octane];
(S)-6-phenyl-3H-1'-azaspiro[imidazo[2,1-b]oxazole-2,3'-bicyclo[2.2.2]octane];
or a pharmaceutically acceptable salt or stereoisomer thereof.

The present application also provides a method for the treatment or alleviation of disorders associated with the nicotinic cholinergic system, especially affective disorders such as schizophrenia, anxiety, mania, manic depression and depression, as well as neurodegenerative disorders such as Alzheimer's disease, Down's syndrome, Parkinson's disease, Huntington's disease and cognitive disorders such as memory impairment, cognition deficits, memory loss and attention deficits and other uses such as treatment of nicotine addiction or neuroinflammation, smoking cessation and analgesia, which comprises administering together with a conventional adjuvant, carrier or diluent a therapeutically effective amount of a compound of Formula I or a stereoisomer thereof, or a pharmaceutically acceptable salt thereof.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, 3-methylbutyl, hexyl and the like. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

"Alkoxy" or "alkyloxy" represents an alkyl group as defined above with the indicated number of carbon atoms attached through an oxygen bridge. Examples of "$C_{1-6}$alkoxy" include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein have an asymmetric center. It is understood, that whether a chiral center in an isomer is "R" or "S" depends on the chemical nature of the substituents of the chiral center. All configurations of compounds of the invention are considered part of the invention. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The enantiomeric forms may also be separated by fractionation through chiral high pressure liquid chromatography columns.

The present invention includes within its scope all possible enantiomeric forms of Formula I, II and III:

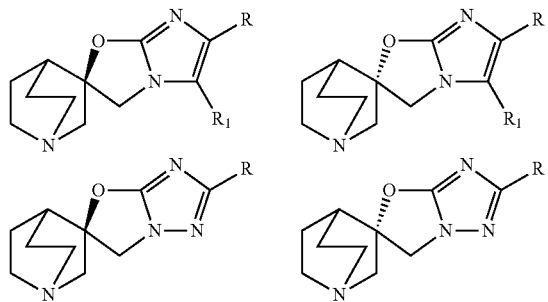

All chiral, diastereomeric, tautomeric forms, racemic forms and all geometric isomeric forms of the compound of Formulas I, II and III are intended, unless the specific stereochemistry or isomeric form is specifically indicated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

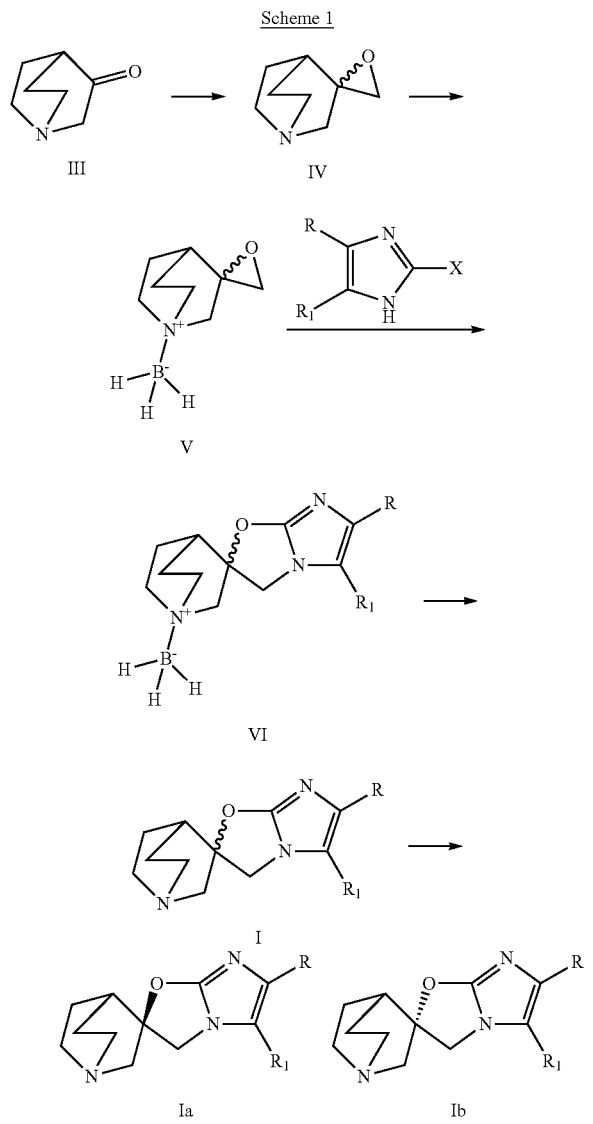

The compound 3-quinuclidinone III can be converted to the known racemic quinuclidine epoxide borane V by known methods (as in WO 9903859). V is then reacted with (substituted) 2-haloimidazoles via treatment with a strong base to give racemic fused compounds VI, which may be deprotected to I by treatment with acid, followed by separation into the two enantiomers Ia and Ib via chiral chromatography.

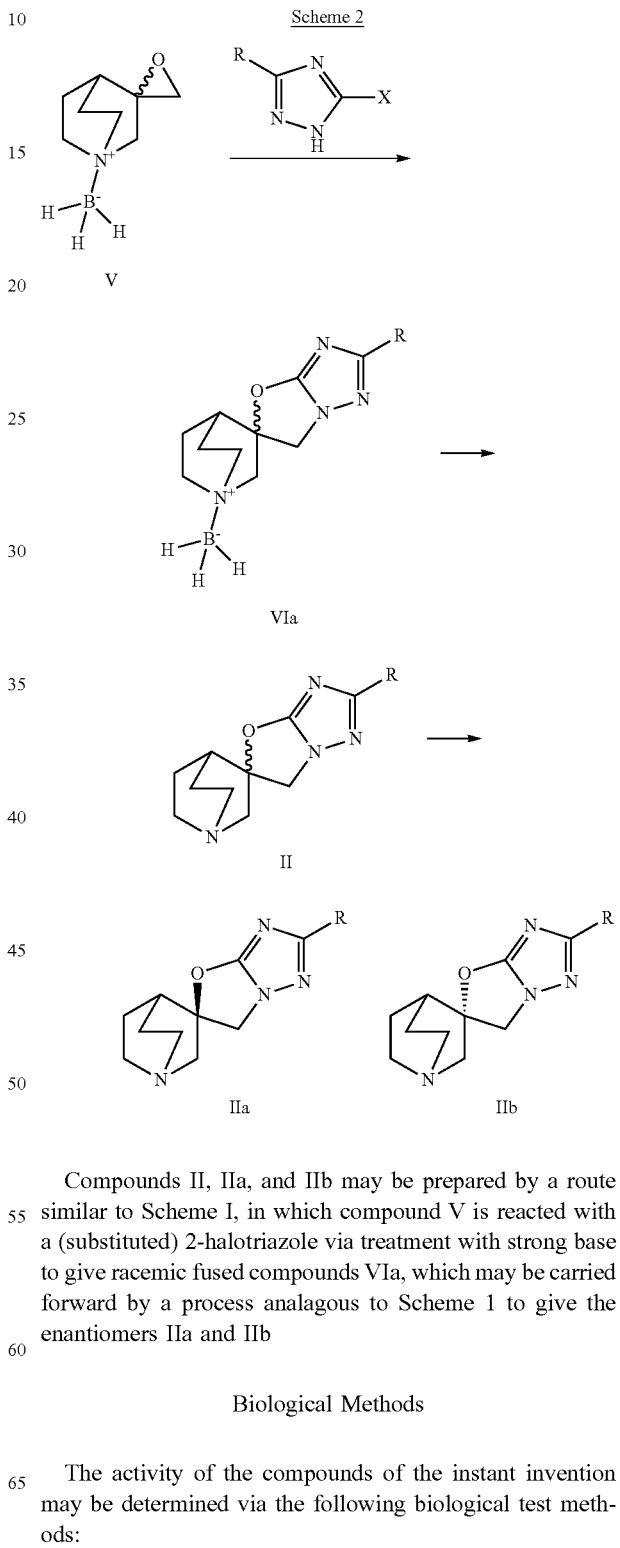

Compounds II, IIa, and IIb may be prepared by a route similar to Scheme I, in which compound V is reacted with a (substituted) 2-halotriazole via treatment with strong base to give racemic fused compounds VIa, which may be carried forward by a process analagous to Scheme 1 to give the enantiomers IIa and IIb Biological Methods The activity of the compounds of the instant invention may be determined via the following biological test methods:

I) α7 Nicotinic Acetylcholine Receptor Binding. Membranes were prepared for binding using HEK293 cells stably expressing the rat α7 nicotinic acetylcholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α-7 for Nicotinic Acetylcholine Receptor Channel Function in Mammalian Cells ("FLIPR").

Summary:

Lead compounds are evaluated for agonist activity at the α7 nicotinic ACh receptor ion channel expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., *Nature Reviews*, 2003, 4:579-586; Gonzalez J. E., et al., *Receptors and Channels*, 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods:

Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo. G418 and Minimal Essential Medium were purchased from InVitrogen Life Technologies, Carlsbad, Calif. Fetal bovine serum was purchased from (InVitrogen, Carlsbad, Calif.).

Cell Culture:

HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ Flux Assays of $Ca^{2+}$ Channels Expressed in HEK-293 Cells:

HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis:

The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos Quantification Assay:

Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminiscence detection kit (catalog #89860, EZ-detect c-Fos Trans kit, Pierce Biotechnology Inc., Rockford, Ill.).

IV) MK-801 Disrupted Set-Shift Assay in Rats:

This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of specific compounds described herein and tested in the above assay (II) is provided in Table 1.

TABLE 1

| Example Number | Structure | Name | FLIPR α7 (EC$_{50}$, nM) | FLIPR α7 activity[a] rating (EC$_{50}$, nM) |
|---|---|---|---|---|
| 1a | 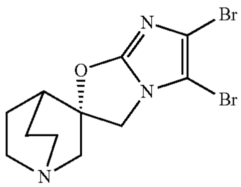 [SMILES: Brc1nc2n(c1Br)C[C@]1(CN3CCC1CC3)O2] | (S)-5,6-Dibromo-3H-1'-azaspiro[imidazo[2,1-b]oxazole-2,3'-bicyclo[2.2.2]octane] | 5690 | + |
| 1b | 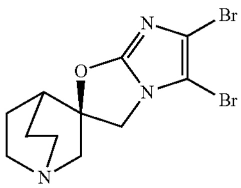 [SMILES: Brc1nc2n(c1Br)C[C@@]1(CN3CCC1CC3)O2] | (R)-5,6-Dibromo-3H-1'-azaspiro[imidazo[2,1-b]oxazole-2,3'-bicyclo[2.2.2]octane] | 19.62 | +++ |
| 2a | 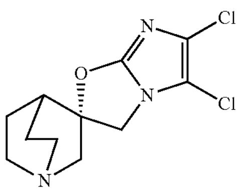 [SMILES: Clc1nc2n(c1Cl)C[C@]1(CN3CCC1CC3)O2] | (S)-5,6-Dichloro-3H-1'-azaspiro[imidazo[2,1-b]oxazole-2,3'-bicyclo[2.2.2]octane] | 1502 | + |
| 2b | 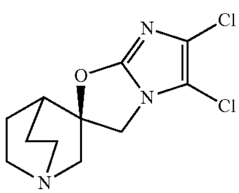 [SMILES: Clc1nc2n(c1Cl)C[C@@]1(CN3CCC1CC3)O2] | (R)-5,6-Dibromo-3H-1'-azaspiro[imidazo[2,1-b]oxazole-2,3'-bicyclo[2.2.2]octane] | 14.2 | +++ |
| 3a | 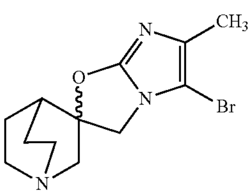 [SMILES: Cc1nc2n(c1Br)CC1(CN3CCC1CC3)O2] | 5-Bromo-6-methyl-3H-1'-azaspiro[imidazo[2,1-b]oxazole-2,3'-bicyclo[2.2.2]octane] | 36.1 | +++ |
| 3b | 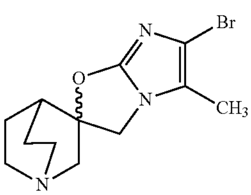 [SMILES: Cc1c(Br)nc2n1CC1(CN3CCC1CC3)O2] | 6-Bromo-5-methyl-3H-1'-azaspiro[imidazo[2,1-b]oxazole-2,3'-bicyclo[2.2.2]octane] | 71.4 | +++ |
| 4a | 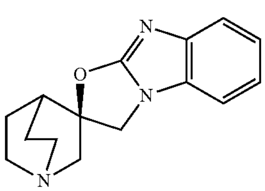 [SMILES: c1ccc2c(c1)nc1n2C[C@@]2(CN3CCC2CC3)O1] | (R)-3H-1'-Azaspiro[benzo[4,5]imidazo[2,1-b]oxazole-2,3'-bicyclo[2.2.2]octane] | 13.6 | +++ |

TABLE 1-continued

| Example Number | Structure | Name | FLIPR α7 (EC$_{50}$, nM) | FLIPR α7 activity[a] rating (EC$_{50}$, nM) |
|---|---|---|---|---|
| 4b | 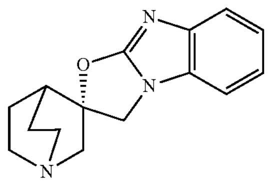 [SMILES: c1ccc2c(c1)nc1n2C[C@]2(CN3CCC2CC3)O1] | (S)-3H-1'-Azaspiro[benzo[4,5]imidazo[2,1-b]oxazole-2,3'-bicyclo[2.2.2]octane] | 6662.0 | + |
| 5a | 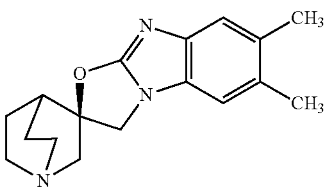 [SMILES: Cc1cc2nc3n(c2cc1C)C[C@@]1(CN2CCC1CC2)O3] | (R)-6,7-Dimethyl-3H-1'-azaspiro[benzo[4,5]imidazo[2,1-b]oxazole-2,3'-bicyclo[2.2.2]octane] | 65.3 | +++ |
| 5b | 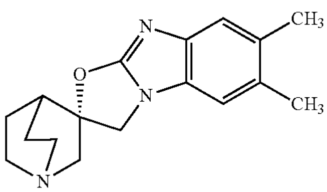 [SMILES: Cc1cc2nc3n(c2cc1C)C[C@]1(CN2CCC1CC2)O3] | (S)-6,7-Dimethyl-3H-1'-azaspiro[benzo[4,5]imidazo[2,1-b]oxazole-2,3'-bicyclo[2.2.2]octane] | >100000 | NA |
| 6a | 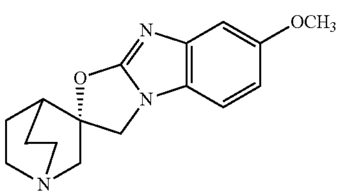 [SMILES: COc1ccc2c(c1)nc1n2C[C@]2(CN3CCC2CC3)O1] | (S)-7-Methoxy-3H-1'-azaspiro[benzo[4,5]imidazo[2,1-b]oxazole-2,3'-bicyclo[2.2.2]octane] | 1434 | + |
| 6b | 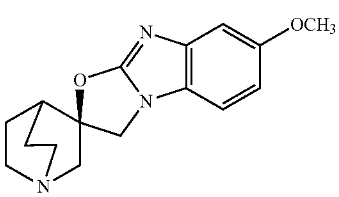 [SMILES: COc1ccc2c(c1)nc1n2C[C@@]2(CN3CCC2CC3)O1] | (R)-7-Methoxy-3H-1'-azaspiro[benzo[4,5]imidazo[2,1-b]oxazole-2,3'-bicyclo[2.2.2]octane] | 10.3 | +++ |
| 7a | 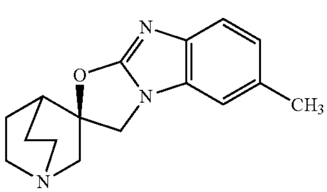 [SMILES: Cc1ccc2nc3n(c2c1)C[C@@]1(CN2CCC1CC2)O3] | (R)-6-Methyl-3H-1'-azaspiro[benzo[4,5]imidazo[2,1-b]oxazole-2,3'-bicyclo[2.2.2]octane] | 35.0 | +++ |
| 7b | 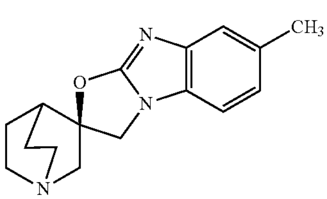 [SMILES: Cc1ccc2c(c1)nc1n2C[C@@]2(CN3CCC2CC3)O1] | (R)-7-Methyl-3H-1'-azaspiro[benzo[4,5]imidazo[2,1-b]oxazole-2,3'-bicyclo[2.2.2]octane] | 5.1 | +++ |

TABLE 1-continued

| Example Number | Structure | Name | FLIPR α7 (EC$_{50}$, nM) | FLIPR α7 activity[a] rating (EC$_{50}$, nM) |
|---|---|---|---|---|
| 8a | 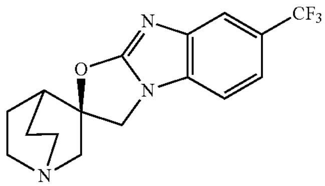 [SMILES: FC(F)(F)c1ccc2c(c1)nc1n2C[C@@]2(CN3CCC2CC3)O1] | (R)-7-(Trifluoromethyl)-3H-1'-azaspiro[benzo[4,5]imidazo[2,1-b]oxazole-2,3'-bicyclo[2.2.2]octane] | 4.7 | +++ |
| 8b | 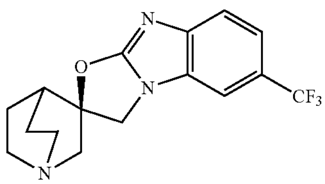 [SMILES: FC(F)(F)c1ccc2nc3n(c2c1)C[C@@]1(CN2CCC1CC2)O3] | (R)-6-(Trifluoromethyl)-3H-1'-azaspiro[benzo[4,5]imidazo[2,1-b]oxazole-2,3'-bicyclo[2.2.2]octane] | 7186.0 | + |
| 8c | 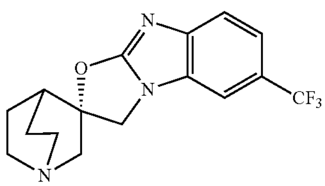 [SMILES: FC(F)(F)c1ccc2nc3n(c2c1)C[C@]1(CN2CCC1CC2)O3] | (S)-6-(Trifluoromethyl)-3H-1'azaspiro[benzo[4,5]imidazo[2,1-b]oxazole-2,3'-bicyclo[2.2.2]octane] | >100000 | NA |
| 8d | 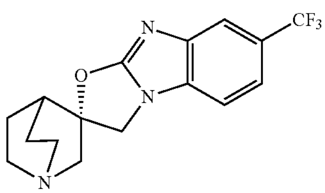 [SMILES: FC(F)(F)c1ccc2c(c1)nc1n2C[C@]2(CN3CCC2CC3)O1] | (S)-7-(Trifluoromethyl)-3H-1'-azaspiro[benzo[4,5]imidazo[2,1-b]oxazole-2,3'-bicyclo[2.2.2]octane] | 1328 | + |
| 9a | 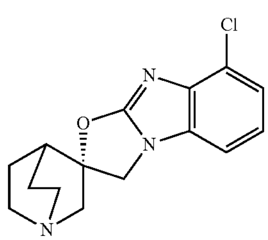 [SMILES: Clc1cccc2c1nc1n2C[C@]2(CN3CCC2CC3)O1] | (S)-8-Chloro-3H-1'-azaspiro[benzo[4,5]imidazo[2,1-b]oxazole-2,3'-bicyclo[2.2.2]octane] | 12110.0 | + |
| 9b | 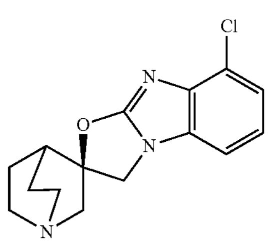 [SMILES: Clc1cccc2c1nc1n2C[C@@]2(CN3CCC2CC3)O1] | (R)-8-Chloro-3H-1'-azaspiro[benzo[4,5]imidazo[2,1-b]oxazole-2,3'-bicyclo[2.2.2]octane] | 24.6 | +++ |

TABLE 1-continued

| Example Number | Structure | Name | FLIPR α7 (EC$_{50}$, nM) | FLIPR α7 activity$^a$ rating (EC$_{50}$, nM) |
|---|---|---|---|---|
| 9c | 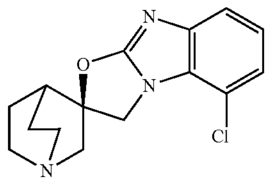 [SMILES: Clc1cccc2nc3n(c12)C[C@@]1(CN2CCC1CC2)O3] | (R)-5-Chloro-3H-1'-azaspiro[benzo[4,5]imidazo[2,1-b]oxazole-2,3'-bicyclo[2.2.2]octane] | 347 | ++ |
| 9d | 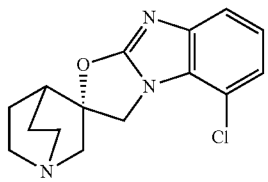 [SMILES: Clc1cccc2nc3n(c12)C[C@]1(CN2CCC1CC2)O3] | (S)-5-Chloro-3H-1'-azaspiro[benzo[4,5]imidazo[2,1-b]oxazole-2,3'-bicyclo[2.2.2]octane] | 3952.0 | + |
| 10a | 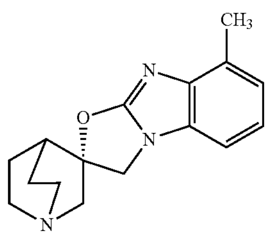 [SMILES: Cc1cccc2c1nc1n2C[C@]2(CN3CCC2CC3)O1] | (S)-8-Methyl-3H-1'-azaspiro[benzo[4,5]imidazo[2,1-b]oxazole-2,3'-bicyclo[2.2.2]octane] | 263 | ++ |
| 10b | 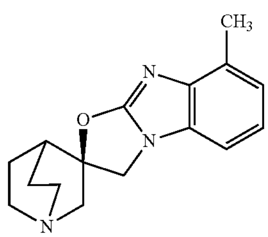 [SMILES: Cc1cccc2c1nc1n2C[C@@]2(CN3CCC2CC3)O1] | (R)-8-Methyl-3H-1'-azaspiro[benzo[4,5]imidazo[2,1-b]oxazole-2,3'-bicyclo[2.2.2]octane] | 9.1 | +++ |
| 11a | 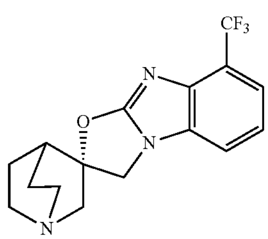 [SMILES: FC(F)(F)c1cccc2c1nc1n2C[C@]2(CN3CCC2CC3)O1] | (S)-8-(Trifluoromethyl)-3H-1'-azaspiro[benzo[4,5]imidazo[2,1-b]oxazole-2,3'-bicyclo[2.2.2]octane] | 32500 | + |
| 11b | 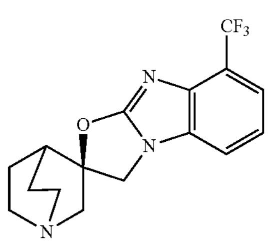 | (R)-8-(Trifluoromethyl)-3H-1'-azaspiro[benzo[4,5]imidazo[2,1-b]oxazole-2,3'-bicyclo[2.2.2]octane] | 22 | +++ |

TABLE 1-continued

| Example Number | Structure | Name | FLIPR α7 (EC$_{50}$, nM) | FLIPR α7 activity[a] rating (EC$_{50}$, nM) |
|---|---|---|---|---|
| 12a | 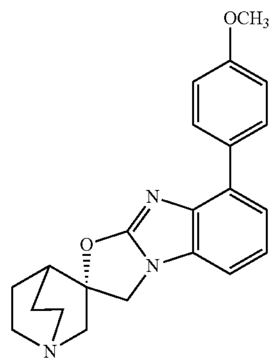 [SMILES: COc1ccc(-c2cccc3c2nc2n3C[C@]3(CN4CCC3CC4)O2)cc1] | (S)-8-(4-Methoxyphenyl)-3H-1'-azaspiro[benzo[4,5]imidazo[2,1-b]oxazole-2,3'-bicyclo[2.2.2]octane] | >100000 | NA |
| 12b | 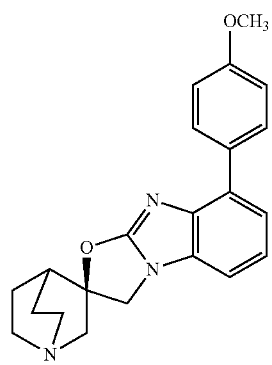 [SMILES: COc1ccc(-c2cccc3c2nc2n3C[C@@]3(CN4CCC3CC4)O2)cc1] | (R)-8-(4-Methoxyphenyl)-3H-1'-azaspiro[benzo[4,5]imidazo[2,1-b]oxazole-2,3'-bicyclo[2.2.2]octane] | 28 | +++ |
| 13a | 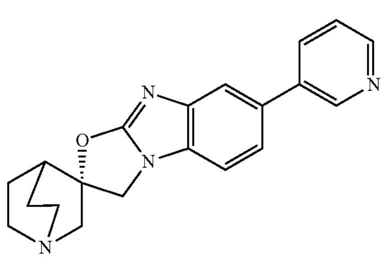 [SMILES: c1cncc(-c2ccc3c(c2)nc2n3C[C@]3(CN4CCC3CC4)O2)c1] | (S)-7-(Pyridin-3-yl)-3H-1'-azaspiro[benzo[4,5]imidazo[2,1-b]oxazole-2,3'-bicyclo[2.2.2]octane] | 2988.0 | + |
| 13b | 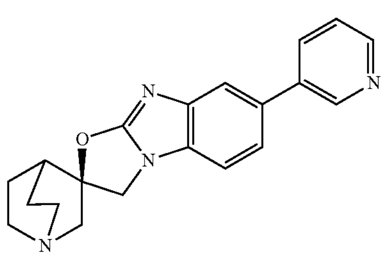 [SMILES: c1cncc(-c2ccc3c(c2)nc2n3C[C@@]3(CN4CCC3CC4)O2)c1] | (R)-7-(Pyridin-3-yl)-3H-1'-azaspiro[benzo[4,5]imidazo[2,1-b]oxazole-2,3'-bicyclo[2.2.2]octane] | 634 | ++ |

TABLE 1-continued

| Example Number | Structure | Name | FLIPR α7 (EC$_{50}$, nM) | FLIPR α7 activity[a] rating (EC$_{50}$, nM) |
|---|---|---|---|---|
| 14a | 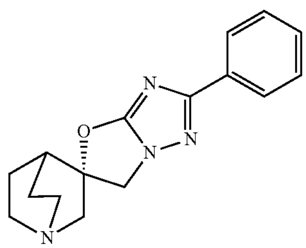 [SMILES: c1ccc(-c2nc3n(n2)C[C@]2(CN4CCC2CC4)O3)cc1] | (S)-2-Phenyl-6H-1'-azaspiro[oxazolo[3,2-b][1,2,4]triazole-5,3'-bicyclo[2.2.2]octane] | 437 | ++ |
| 14b | 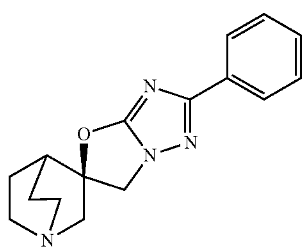 [SMILES: c1ccc(-c2nc3n(n2)C[C@@]2(CN4CCC2CC4)O3)cc1] | (R)-2-Phenyl-6H-1'-azaspiro[oxazolo[3,2-b][1,2,4]triazole-5,3'-bicyclo[2.2.2]octane] | 4.1 | +++ |
| 15 | 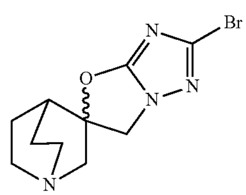 [SMILES: Brc1nc2n(n1)CC1(CN3CCC1CC3)O2] | 2-Bromo-6H-1'-azaspiro[oxazolo[3,2-b][1,2,4]triazole-5,3'-bicyclo[2.2.2]octane] | 362 | ++ |
| 16 | 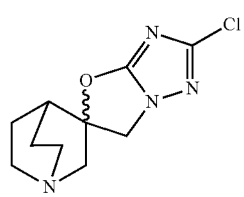 [SMILES: Clc1nc2n(n1)CC1(CN3CCC1CC3)O2] | 2-Chloro-6H-1'-azaspiro[oxazolo[3,2-b][1,2,4]triazole-5,3'-bicyclo[2.2.2]octane] | 174 | ++ |
| 17 | 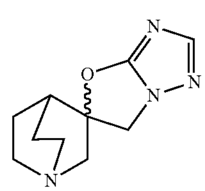 [SMILES: c1nc2n(n1)CC1(CN3CCC1CC3)O2] | 6H-1'-Azaspiro[oxazolo[3,2-b][1,2,4]triazole-5,3'-bicyclo[2.2.2]octane] | 321 | ++ |
| 18 | 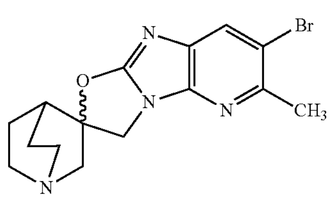 [SMILES: Cc1nc2c(cc1Br)nc1n2CC2(CN3CCC2CC3)O1] | 7-Bromo-6-methyl-3H-1'-azaspiro[oxazolo[2',3':2,3]imidazo[4,5-b]pyridine-2,3'-bicyclo[2.2.2]octane] | 967 | ++ |

TABLE 1-continued

| Example Number | Structure | Name | FLIPR α7 (EC$_{50}$, nM) | FLIPR α7 activity[a] rating (EC$_{50}$, nM) |
|---|---|---|---|---|
| 19 | 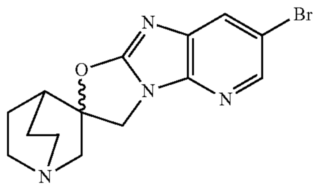 [SMILES: Brc1cnc2c(c1)nc1n2CC2(CN3CCC2CC3)O1] | 7-Bromo-3H-1'-azaspiro[oxazolo[2',3':2,3]imidazo[4,5-b]pyridine-2,3'-bicyclo[2.2.2]octane] | 49 | +++ |
| 20 | 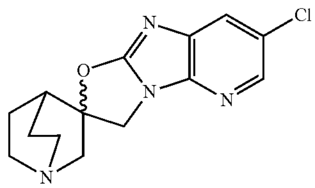 [SMILES: Clc1cnc2c(c1)nc1n2CC2(CN3CCC2CC3)O1] | 7-Chloro-3H-1'-azaspiro[oxazolo[2',3':2,3]imidazo[4,5-b]pyridine-2,3'-bicyclo[2.2.2]octane] | 66 | +++ |
| 21a | 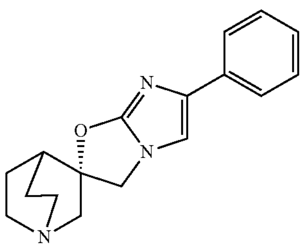 [SMILES: c1ccc(-c2cn3c(n2)O[C@@]2(CN4CCC2CC4)C3)cc1] | (S)-6-Phenyl-3H-1'-azaspiro[imidazo[2,1-b]oxazole-2,3'-bicyclo[2.2.2]octane] | 10 | +++ |
| 21b | 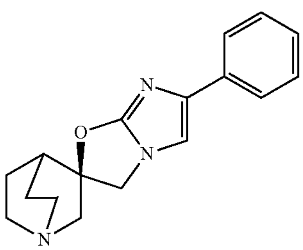 [SMILES: c1ccc(-c2cn3c(n2)O[C@]2(CN4CCC2CC4)C3)cc1] | (R)-6-Phenyl-3H-1'-azaspiro[imidazo[2,1-b]oxazole-2,3'-bicyclo[2.2.2]octane] | 53 | +++ |

[a]Activity based on EC$_{50}$ nM values: +++ = <100 nM; ++ = 100-1000 nM; + = 1000-100000 nM;
[b]NT = Not tested; NA = Not active (>1000000 nM).

Pharmaceutical Compositions and Methods of Treatment

Compounds of formula I bind to alpha 7 and can be useful in treating affective disorders and neurodegenerative disorders. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of affective disorders or neurodegenerative disorders.

Another aspect of the invention is the use of a compound of formula I in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

Another aspect of the invention is a method of treating cognitive disorders comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butyloxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

$^1$H-NMR spectra were run on a Bruker 500, 400, or 300 MHz instrument and chemical shifts were reported in ppm (δ) with reference to tetramethylsilane (δ=0.0). All evaporations were carried out under reduced pressure. Unless otherwise stated, LC/MS analyses were carried out on a Shimadzu instrument using a Phenomenex-Luna 4.6×50 mm S 10 reverse phase column employing a flow rate of 4 mL/min using a 0.1% TFA in methanol/water gradient [0-100% in 3 min, with 4 min run time] and a UV detector set at 220 nm or Gemini C18 4.6×50 mm 5 u reverse phase column employing a flow rate of 5 mL/min using a 10 mM ammonium acetate acetonitrile/water gradient [5-95% in 3 min, with 4 min run time] and a UV detector set at 220 nm (negative-ion mass spectrometry). Unless otherwise stated, purification could be done by preparative C-18 column employing gradients of methanol-water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient. Optical Rotations were performed in MeOH in a 50 mm cell at 20° C. set at a wavelength of 589 nm.

REFERENCE EXAMPLE 1

1'-Azaspiro[oxirane-2,3'-bicyclo[2.2.2]octan]-1'yl-4-iumtrihydroborate

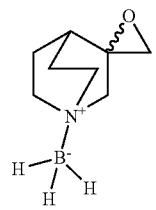

1'-Azaspiro[oxirane-2,3'-bicyclo[2.2.2]octan]-1'yl-4-iumtrihydroborate was synthesized according to WO9903859. The product obtained after drying was a white solid. The product was used in the next step without any further characterization.

EXAMPLE 1

(R)-5,6-Dibromo-3H-1'-azaspiro[imidazo[2,1-b]oxazole-2,3'-bicyclo[2.2.2]octane] and (S)-5,6-dibromo-3H-1'-azaspiro[imidazo[2,1-b]oxazole-2,3'-bicyclo[2.2.2]octane]

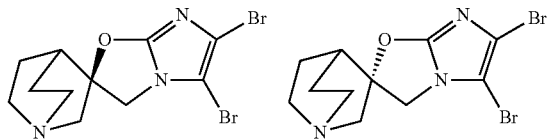 [SMILES: Brc1nc2n(c1Br)C[C@@]1(CN3CCC1CC3)O2 ; Brc1nc2n(c1Br)C[C@]1(CN3CCC1CC3)O2]

Step A: (5,6-Dibromo-3H-1'-azaspiro[imidazo[2,1-b]oxazole-2,3'-bicyclo[2.2.2]octan]-1'-yl-8-ium)trihydroborate

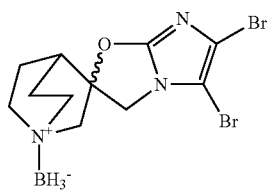

To 2,4,5-tribromo-1H-imidazole (2 g, 6.6 mmol) in THF (15 mL) was added N-butyllithium (2.6 mL, 6.6 mmol) dropwise at −78° C. After 45 minutes, a solution of racemic (1'-azaspiro[oxirane-2,3'-bicyclo[2.2.2]octan]-1'-yl-4-iumtrihydroborate (2.0 g, 13 mmol) from the reference example, in THF (15 mL) was added dropwise at −78° C. The cooling bath was removed and the reaction mixture warmed to room temperature. After 15 minutes, the mixture was heated to 70° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (biotage) to yield racemic (5,6-dibromo-3H-1'-azaspiro[imidazo[2,1-b]oxazole-2,3'-bicyclo[2.2.2]octan]-1'-yl-8-ium)trihydroborate (2.1 g, 5.6 mmol, 85% yield) as a white powder. $^1$H NMR (500 MHz, DMSO-d$_6$) δ 4.34 (d, J=9.9 Hz, 1H), 4.22 (d, J=9.9 Hz, 1H), 3.37 (dd, J=15.3, 2.5 Hz, 1H), 3.22 (dd, J=15.3, 2.1 Hz, 1H), 3.07-2.96 (m, 1H), 2.94-2.77 (m, 3H), 2.40 (br. s., 1H), 2.04-1.93 (m, 1H), 1.86-1.72 (m, 3H), 1.65-0.97 (m, 3H). MS (LC/MS) R.T.=3.33; [M-BH$_3$]$^+$=363.95.

Step B: (R)-5,6-Dibromo-3H-1'-azaspiro[imidazo[2,1-b]oxazole-2,3'-bicyclo[2.2.2]octane] and (S)-5,6-dibromo-3H-1'-azaspiro[imidazo[2,1-b]oxazole-2,3'-bicyclo[2.2.2]octane]

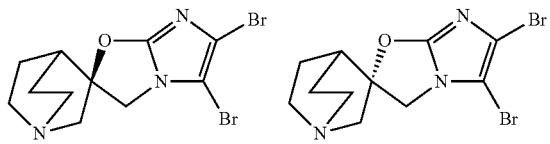 [SMILES: Brc1nc2n(c1Br)C[C@@]1(CN3CCC1CC3)O2 ; Brc1nc2n(c1Br)C[C@]1(CN3CCC1CC3)O2]

The racemic (5,6-dibromo-3H-1'-azaspiro[imidazo[2,1-b]oxazole-2,3'-bicyclo[2.2.2]octan]-1'-yl-8-ium)trihydroborate (0.21 g, 0.56 mmol), from example 1, step A was separated using a chiral column, (Chiralpak AD 21×250 mm 10 u, inj. vol. 2000 uL, Isocratic, start % B: 35, flow rate 15 mL/min., solvent A: 0.1% diethylamine/heptane, solvent B: ethanol, wavelength 220 nm) to yield two enantiomers (enantiomer 1 and enantiomer 2). To enantiomer 1, first off the column, in acetone (5 mL) was added 3 M HCl (0.37 mL, 1.1 mmol) at room temperature. After 35 minutes, 1 N NaOH was added until the pH was ~8-9. The product was extracted with ethyl acetate, dried with MgSO$_4$, filtered and the solvent was removed to yield (S)-5,6-dibromo-3H-1'-azaspiro[imidazo[2,1-b]oxazole-2,3'-bicyclo[2.2.2]octane] (0.10 g, 0.26 mmol, 46.5% yield). $^1$H NMR (500 MHz, DMSO-d$_6$) δ 4.33 (d, J=9.8 Hz, 1H), 4.13 (d, J=9.8 Hz, 1H), 3.16-3.05 (m, 2H), 2.82-2.70 (m, 2H), 2.68-2.60 (m, 2H), 2.26-2.16 (m, 1H), 1.91-1.76 (m, 1H), 1.61 (d, J=3.4 Hz, 2H), 1.52-1.40 (m, 1H). LC/MS RT=2.11 [M]$^+$=363.95. Optical Rotation=+36.83°. To enantiomer 2, second off the column, in acetone (5 mL) was added 3 M HCl (0.37 mL, 1.11 mmol) at room temperature. After 35 minutes, 1 N NaOH was added until the pH was ~8-9. The product was extracted with ethyl acetate, dried with MgSO$_4$, filtered and the solvent was removed to yield (R)-5,6-dibromo-3H-1'-azaspiro[imidazo[2,1-b]oxazole-2,3'-bicyclo[2.2.2]octane] (0.097 g, 0.25 mmol, 45.1% yield). $^1$H NMR (500 MHz, DMSO-d$_6$) δ 4.34 (d, J=9.8 Hz, 1H), 4.13 (d, J=9.8 Hz, 1H), 3.18-3.05 (m, 2H), 2.86-2.70 (m, 2H), 2.71-2.60 (m, 2H), 2.24-2.14 (m, 1H), 1.91-1.73 (m, 1H), 1.65-1.53 (m, 2H), 1.53-1.34 (m, 1H). LC/MS RT=2.11 [M]$^+$=363.95. Optical Rotation=−33.24°.

EXAMPLE 2

(R)-5,6-Dichloro-3H-1'-azaspiro[imidazo[2,1-b]oxazole-2,3'-bicyclo[2.2.2]octane] and (S)-5,6-dichloro-3H-1'-azaspiro[imidazo[2,1-b]oxazole-2,3'-bicyclo [2.2.2]octane]

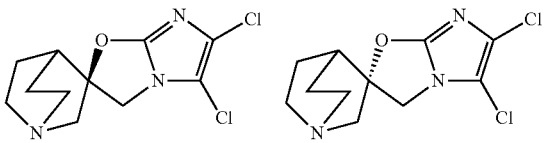 [SMILES: Clc1nc2n(c1Cl)C[C@@]1(CN3CCC1CC3)O2 ; Clc1nc2n(c1Cl)C[C@]1(CN3CCC1CC3)O2]

Step A: (5,6-Dichloro-3H-1'-azaspiro[imidazo[2,1-b]oxazole-2,3'-bicyclo[2.2.2]octan]-1'-yl-8-ium)trihydroborate

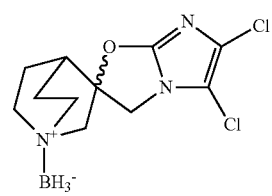

To 2-bromo-4,5-dichloro-1H-imidazole (1 g, 4.6 mmol) in THF (25 mL) was added N-butyllithium (1.85 mL, 4.6 mmol) dropwise at −78° C. After 45 minutes, a solution of racemic (1'-azaspiro[oxirane-2,3'-bicyclo[2.2.2]octan]-1'-yl-4-ium)trihydroborate (0.99 g, 6.5 mmol) from the reference example, in THF (15 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield racemic (5,6-dichloro-3H-1'-azaspiro[imidazo[2,1-b]oxazole-2,3'-bicyclo[2.2.2]octan]-1'-yl-8-ium)trihydroborate as a solid. LC/MS RT=2.96 [M+1-BH$_3$]$^+$=274.01.

Step B: (R)-5,6-Dichloro-3H-1'-azaspiro[imidazo[2,1-b]oxazole-2,3'-bicyclo[2.2.2]octane] and (S)-5,6-dichloro-3H-1'-azaspiro[imidazo[2,1-b]oxazole-2,3'-bicyclo[2.2.2]octane]

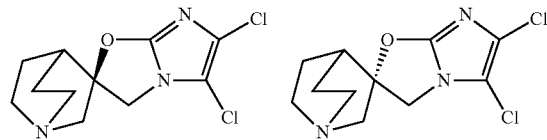 [SMILES: Clc1nc2n(c1Cl)C[C@@]1(CN3CCC1CC3)O2 ; Clc1nc2n(c1Cl)C[C@]1(CN3CCC1CC3)O2]

To racemic (5,6-dichloro-3H-1'-azaspiro[imidazo[2,1-b]oxazole-2,3'-bicyclo[2.2.2]octan]-1'-yl-8-ium)trihydroborate (0.39 g, 1.4 mmol), from example 2, step A, in acetone (5 mL) was added 3 M HCl (0.9 mL, 2.7 mmol). After 45 minutes, the reaction was neutralized with 1 N NaOH until the pH was ~8-9. The resulting solution was extracted with ethyl acetate followed by chloroform. The organics were combined, dried with MgSO$_4$, filtered and the solvent was removed to yield the crude material. The product was purified by chromatography (Biotage) to yield racemic 5,6-dichloro-3H-1'-azaspiro[imidazo[2,1-b]oxazole-2,3'-bicyclo[2.2.2]octane] (0.22 g, 0.8 mmol, 58.7% yield) as a white powder. $^1$H NMR (500 MHz, DMSO-d$_6$) δ 4.37 (d, J=9.6 Hz, 1H), 4.15 (d, J=9.8 Hz, 1H), 3.19-3.03 (m, 2H), 2.84-2.69 (m, 2H), 2.69-2.60 (m, 2H), 2.21 (quin, J=3.0 Hz, 1H), 1.90-1.74 (m, 1H), 1.69-1.54 (m, 2H), 1.51-1.30 (m, 1H). LC/MS RT=1.92 [M+1]$^+$=274.01.

The enantiomers were separated on a Chiralcel OJ column (conditions: Chiralcel OJ 21×250 mm column, 12% ethanol: 88% (0.1% diethylamine in heptane); flow rate 15 mL/min; peaks center at 12.2 and 15.4 min). Peak 1: 111 mg white solid. MS (LC/MS; column: X-Bridge C-18 2.1×50 mm; 3.5 uM) R.T.=2.11; [M+1]$^+$=274.03; Chiral HPLC (column: Chiralcel OD-H, 4.6×100 mm, 5 uM; 20% ethanol/80% (0.1% diethylamine/heptane)); RT 4.36 min; $^1$H NMR (500 MHz, DMSO-d$_6$) δ ppm 1.41-1.53 (m, 1H) 1.56-1.66 (m, 2H) 1.77-1.90 (m, 1H) 2.17-2.23 (m, 1H) 2.62-2.70 (m, 2H) 2.71-2.85 (m, 2H) 3.12 (s, 2H) 4.16 (d, J=9.77 Hz, 1H) 4.38 (d, J=9.61 Hz, 1H)

Peak 2: 112 mg white solid. MS (LC/MS; column: X-Bridge C-18 2.1×50 mm; 3.5 uM) R.T.=2.24; [M+1]$^+$=274.01; Chiral HPLC (column: Chiralcel OD-H, 4.6×100 mm, 5 uM; 20% ethanol/80% (0.1% diethylamine/heptane)); RT 2.78 min; $^1$H NMR (500 MHz, DMSO-d$_6$) δ ppm 1.42-1.54 (m, 1H) 1.56-1.63 (m, 1H) 1.77-1.89 (m, 1H) 2.14-2.25 (m, 1H) 2.67 (br. s., 2H) 2.71-2.85 (m, 2H) 3.12 (s, 2H) 4.16 (d, J=9.61 Hz, 1H) 4.38 (d, J=9.77 Hz, 1H)

EXAMPLE 3

5-Bromo-6-methyl-3H-1'-azaspiro[imidazo[2,1-b]oxazole-2,3'-bicyclo[2.2.2]octane] and 6-bromo-5-methyl-3H-1'-azaspiro[imidazo[2,1-b]oxazole-2,3'-bicyclo[2.2.2]octane]

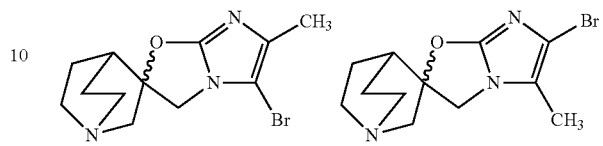

Step A: (5-Bromo-6-methyl-3H-1'-azaspiro[imidazo[2,1-b]oxazole-2,3'-bicyclo[2.2.2]octan]-1'-yl-8-ium)trihydroborate and (6-bromo-5-methyl-3H-1'-azaspiro[imidazo[2,1-b]oxazole-2,3'-bicyclo[2.2.2]octan]-1'-yl-8-ium)trihydroborate

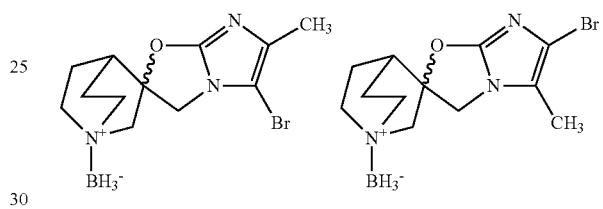

To 2,4-dibromo-5-methyl-1H-imidazole (0.8 g, 3.3 mmol) in THF (25 mL) was added N-butyllithium (1.3 mL, 3.3 mmol) dropwise at −78° C. After 45 minutes, a solution of racemic 1'-azaspiro[oxirane-2,3'-bicyclo[2.2.2]octan]-1'-yl-4-ium)trihydroborate (0.56 g, 3.7 mmol) from the reference example, in THF (20 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield the regioisomeric products. These regioisomers were separated by reverse phase chromatography using a Sunfire column with gradients of acetonitrile-water containing 0.1% of trifluoroacetic acid (TFA), and at 40 mL/min flow rate. The pure fractions for peak 1 and peak 2 were then neutralized with 1 N NaOH (pH ~8-9) and the products were extracted with ethyl acetate. The organic layers were dried with MgSO$_4$, filtered and the solvent was removed to yield racemic (5-bromo-6-methyl-3H-1'-azaspiro[imidazo[2,1-b]oxazole-2,3'-bicyclo[2.2.2]octan]-1'-yl-8-ium)trihydroborate (0.32 g, 1.0 mmol, 30.8% yield) $^1$H NMR (500 MHz, DMSO-d$_6$) δ 4.23 (d, J=9.8 Hz, 1H), 4.12 (d, J=9.9 Hz, 1H), 3.36 (dd, J=15.2, 2.5 Hz, 1H), 3.19 (dd, J=15.3, 2.1 Hz, 1H), 3.04-2.95 (m, 1H), 2.91-2.73 (m, 3H), 2.35 (br. s., 1H), 2.03-1.88 (m, 4H), 1.84-1.67 (m, 3H), 1.64-1.11 (m, 3H). MS (LC/MS) R.T.=2.09; [M+2]$^+$=300.04 and racemic (6-bromo-5-methyl-3H-1'-azaspiro[imidazo[2,1-b]oxazole-2,3'-bicyclo[2.2.2]octan]-1'-yl-8-ium)trihydroborate (0.33 g, 1.1 mmol, 31.7% yield) as powders. $^1$H NMR (500 MHz, DMSO-d$_6$) δ 4.32 (d, J=10.1 Hz, 1H), 4.12 (d, J=10.2 Hz, 1H), 3.36 (d, J=2.4 Hz, 1H), 3.18 (dd, J=15.2, 2.2 Hz, 1H), 2.99 (d, J=2.9 Hz, 1H), 2.93-2.78 (m, 3H), 2.31 (d, J=2.0 Hz, 1H), 2.06-1.94 (m, 4H), 1.84-1.69 (m, 3H), 1.62-1.22 (m, 3H). MS (LC/MS) R.T.=2.64; [M+2]$^+$=300.04.

Step B: 5-Bromo-6-methyl-3H-1'-azaspiro[imidazo[2,1-b]oxazole-2,3'-bicyclo[2.2.2]octane]

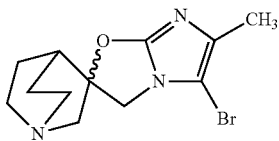 [SMILES: Cc1nc2n(c1Br)CC1(CN3CCC1CC3)O2]

To racemic (5-bromo-6-methyl-3H-1'-azaspiro[imidazo[2,1-b]oxazole-2,3'-bicyclo[2.2.2]octan]-1'-yl-8-ium)trihydroborate (0.3 g, 0.96 mmol), regioisomer 1 from example 3, step A, in acetone (5 mL) was added 3 M HCl (0.64 mL, 1.9 mmol) at room temperature. After 35 minutes, 1 N NaOH was added until the pH was ~8-9. The product was extracted with ethyl acetate, dried with MgSO$_4$, filtered and the solvent was removed to yield racemic 5-bromo-6-methyl-3H-1'-azaspiro[imidazo[2,1-b]oxazole-2,3' bicyclo[2.2.2]octane] (0.2 g, 0.67 mmol, 69.8% yield). $^1$H NMR (500 MHz, DMSO-d$_6$) δ 4.22 (d, J=9.6 Hz, 1H), 4.02 (d, J=9.6 Hz, 1H), 3.15-3.03 (m, 2H), 2.81-2.72 (m, 2H), 2.69-2.61 (m, 2H), 2.21-2.13 (m, 1H), 1.99-1.91 (m, 3H), 1.86 (dd, J=12.6, 9.4 Hz, 1H), 1.60 (ddd, J=10.1, 5.0, 3.2 Hz, 2H), 1.51-1.39 (m, 1H). MS (LC/MS) R.T.=1.16; [M+1]$^+$=299.9

Step B: 6-Bromo-5-methyl-3H-1'-azaspiro[imidazo[2,1-b]oxazole-2,3'-bicyclo[2.2.2]octane]

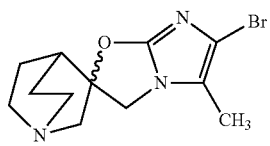 [SMILES: Cc1c(Br)nc2n1CC1(CN3CCC1CC3)O2]

To racemic (6-bromo-5-methyl-3H-1'-azaspiro[imidazo[2,1-b]oxazole-2,3'-bicyclo[2.2.2]octan]-1'-yl-8-ium)trihydroborate (0.3 g, 0.96 mmol), regioisomer 2 from example 3, step A, in acetone (5 mL) was added 3 M HCl (0.64 mL, 1.9 mmol) at room temperature. After 35 minutes, 1 N NaOH was added until the pH was ~8-9. The product was extracted with ethyl acetate, dried with MgSO$_4$, filtered and the solvent was removed to yield racemic 6-bromo-5-methyl-3H-1'-azaspiro[imidazo[2,1-b]oxazole-2,3'-bicyclo[2.2.2]octane] (0.27 g, 0.86 mmol, 89% yield). $^1$H NMR (500 MHz, DMSO-d$_6$) δ 4.30 (d, J=9.9 Hz, 1H), 4.02 (d, J=9.9 Hz, 1H), 3.07 (s, 2H), 2.82-2.72 (m, 2H), 2.70-2.61 (m, 2H), 2.12 (t, J=2.8 Hz, 1H), 2.05-2.00 (m, 3H), 1.93-1.80 (m, 1H), 1.65-1.54 (m, 2H), 1.46 (dd, J=10.0, 3.0 Hz, 1H) MS (LC/MS) R.T.=1.89; [M+1]$^+$=299.98

EXAMPLE 4

(R)-3H-1'-Azaspiro[benzo[4,5]imidazo[2,1-b]oxazole-2,3'-bicyclo[2.2.2]octane] and (S)-3H-1'-azaspiro[benzo [4,5]imidazo[2,1-b]oxazole-2,3'-bicyclo[2.2.2]octane]

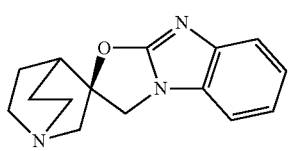

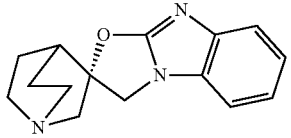

Step A: (3H-1'-Azaspiro[benzo[4,5]imidazo[2,1-b]oxazole-2,3'-bicyclo[2.2.2]octan]-1'-yl-8-ium)trihydroborate

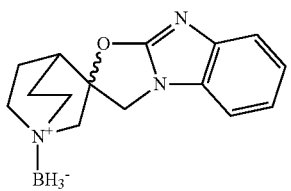

To 2-bromo-1H-benzo[d]imidazole (0.75 g, 3.8 mmol) in THF (25 mL) was added n-butyllithium (1.5 mL, 3.8 mmol) dropwise at −78° C. After 45 minutes, a solution of racemic (1'-azaspiro[oxirane-2,3'-bicyclo[2.2.2]octan]-1'-yl-4-ium) trihydroborate (0.7 g, 4.6 mmol) from the reference example, in THF (15 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield racemic (3H-1'-azaspiro[benzo[4,5]imidazo[2,1-b]oxazole-2,3'-bicyclo[2.2.2]octan]-1'-yl-10-ium)trihydroborate (0.66 g, 2.5 mmol, 64.4% yield) as a white powder. $^1$H NMR (500 MHz, DMSO-d$_6$) δ 7.44-7.34 (m, 1H), 7.31-7.19 (m, 1H), 7.18-6.97 (m, 2H), 4.53 (d, J=9.8 Hz, 1H), 4.31 (d, J=9.8 Hz, 1H), 3.45 (dd, J=15.3, 2.5 Hz, 1H), 3.36-3.29 (m, 1H), 3.09-3.01 (m, 1H), 2.99-2.83 (m, 3H), 2.43 (br. s., 1H), 2.15-2.04 (m, 1H), 1.92-1.75 (m, 3H), 1.69-1.20 (m, 3H). MS (LC/MS) R.T.=2.09; [M+1-BH3]$^+$=256.12.

Step B: (R)-3H-1'-Azaspiro[benzo[4,5]imidazo[2,1-b]oxazole-2,3'-bicyclo[2.2.2]octane] and (S)-3H-1'-azaspiro[benzo[4,5]imidazo[2,1-b]oxazole-2,3'-bicyclo[2.2.2]octane]

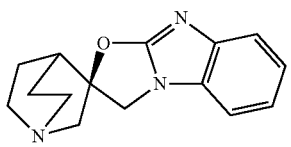

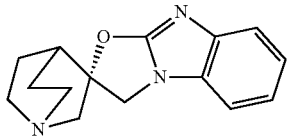

To racemic (3H-1'-azaspiro[benzo[4,5]imidazo[2,1-b]oxazole-2,3'-bicyclo[2.2.2]octan]-1'-yl-10-ium)trihydroborate (0.59 g, 2.2 mmol) from example 4, step A, in acetone (5 mL) was added 3 M HCl (1.5 mL, 4.4 mmol) at room temperature. After 45 minutes, the reaction mixture was neutralized with 1 N NaOH to pH ~8-9. The aqueous solution was extracted with ethyl acetate and then chloroform. The organics were combined, dried with MgSO$_4$, filtered, and the solvent was removed to yield racemic 3H-1'-azaspiro[benzo[4,5]imidazo[2,1-b]oxazole-2,3'-bicyclo[2.2.2]octane] (0.52 g, 2.0 mmol, 92% yield) as a white powder. $^1$H NMR (500 MHz, DMSO-d$_6$) δ 7.45-7.32 (m, 1H), 7.30-7.19 (m, 1H), 7.16-6.93 (m, 2H), 4.50 (d, J=9.6 Hz, 1H), 4.22 (d, J=9.6 Hz, 1H), 3.23-3.10 (m, 2H), 2.82 (t, J=7.8 Hz, 2H), 2.77-2.64 (m, 2H), 2.28-2.16 (m, 1H), 2.00-1.82 (m, 1H), 1.73-1.61 (m, 2H), 1.58-1.46 (m, 1H). MS (LC/MS) R.T.=1.35; [M+1]$^+$=256.16. The racemic material (0.49 g, 1.92 mmol) was separated using a chiral column (Chiralcel OD 21×250 mm 10 u, inj. vol. 2000 uL, isocratic, start % B: 50, flow rate: 15 mL/min, run time: 22 min., solvent A: 0.1% diethylamine/heptane, solvent B: ethanol, wavelength: 220 nM). The pure fractions of enantiomer 1, RT=5.66 min. were combined and the solvent was removed to yield (S)-3H-1'-azaspiro[benzo[4,5]imidazo[2,1-b]oxazole-2,3'-bicyclo[2.2.2]octane] (0.18 g, 0.7 mmol, 37% yield). $^1$H NMR (500 MHz, DMSO-d$_6$) δ 7.46-7.30 (m, 1H), 7.32-7.19 (m, 1H), 7.14-6.98 (m, 2H), 4.50 (d, J=9.5 Hz, 1H), 4.22 (d, J=9.6 Hz, 1H), 3.19 (s, 2H), 2.82 (t, J=7.8 Hz, 2H), 2.75-2.62 (m, 2H), 2.25-2.16 (m, 1H), 2.02-1.86 (m, 1H), 1.75-1.60 (m, 2H), 1.58-1.40 (m, 1H). MS (LC/MS) R.T.=1.33; [M+1]$^+$=256.09. Optical Rotation=+42.41°. The pure fractions of enantiomer 2, RT=7.90 min. were combined and the solvent was removed to yield (R)-3H-1'-azaspiro[benzo[4,5]imidazo[2,1-b]oxazole-2,3'-bicyclo[2.2.2]octane] (0.19 g, 0.74 mmol, 39% yield). $^1$H NMR (500 MHz, DMSO-d$_6$) δ 7.40-7.32 (m, 1H), 7.29-7.20 (m, 1H), 7.15-7.00 (m, 2H), 4.50 (d, J=9.6 Hz, 1H), 4.22 (d, J=9.6 Hz, 1H), 3.24-3.12 (m, 2H), 2.82 (t, J=7.8 Hz, 2H), 2.75-2.65 (m, 2H), 2.28-2.15 (m, 1H), 2.00-1.87 (m, 1H), 1.72-1.60 (m, 2H), 1.57-1.22 (m, 1H). MS (LC/MS) R.T.=1.31; [M+1]$^+$=256.11. Optical Rotation=−41.99°.

EXAMPLE 5

(R)-6,7-Dimethyl-3H-1'-azaspiro[benzo[4,5]imidazo[2,1-b]oxazole-2,3'-bicyclo[2.2.2]octane] and (S)-6,7-dimethyl-3H-1'-azaspiro[benzo[4,5]imidazo[2,1-b]oxazole-2,3'-bicyclo[2.2.2]octane]

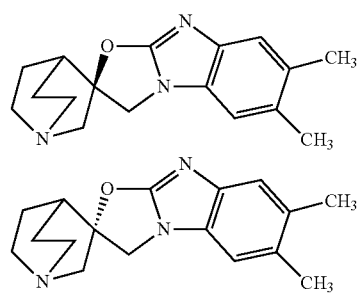

Step A: 6,7-Dimethyl-3H-1'-azaspiro[benzo[4,5]imidazo[2,1-b]oxazole-2,3'-bicyclo[2.2.2]octan]-1'-yl-8-ium)trihydroborate

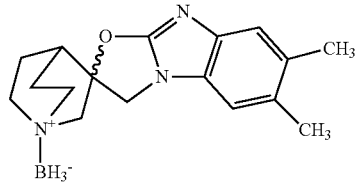

To 2-chloro-5,6-dimethyl-1H-benzo[d]imidazole (0.5 g, 2.8 mmol) in THF (15 mL) was added n-butyllithium (1.10 mL, 2.8 mmol) dropwise at −78° C. After 45 minutes, a solution of racemic (1'-azaspiro[oxirane-2,3'-bicyclo[2.2.2]octan]-1'-yl-4-ium)trihydroborate (0.47 g, 3.0 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The product was purified by chromatography (Biotage) to yield racemic (6,7-dimethyl-3H-1'-azaspiro[benzo[4,5]imidazo[2,1-b]oxazole-2,3'-bicyclo[2.2.2]octan]-1'-yl-10-ium)trihydroborate (0.7 g, 2.3 mmol, 83% yield) as a racemate. $^1$H NMR (500 MHz, DMSO-d$_6$) δ 7.16 (s, 1H), 7.04 (s, 1H), 4.45 (d, J=9.8 Hz, 1H), 4.23 (d, J=9.8 Hz, 1H), 3.43 (dd, J=15.3, 2.3 Hz, 1H), 3.33-3.24 (m, 1H), 3.07-3.00 (m, 1H), 2.97-2.80 (m, 3H), 2.39 (br. s., 1H), 2.26 (d, J=10.2 Hz, 6H), 2.12-2.02 (m, 1H), 1.94-1.73 (m, 3H), 1.46 (br. s., 3H). MS (LC/MS) R.T.=2.53; [M+1-BH3]$^+$=284.11.

Step B: (R)-6,7-Dimethyl-3H-1'-azaspiro[benzo[4,5]imidazo[2,1-b]oxazole-2,3'-bicyclo[2.2.2]octane] and (S)-6,7-dimethyl-3H-1'-azaspiro[benzo[4,5]imidazo[2,1-b]oxazole-2,3'-bicyclo[2.2.2]octane]

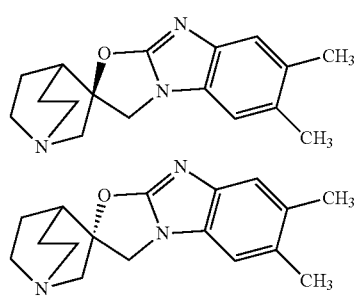

To racemic (6,7-dimethyl-3H-1'-azaspiro[benzo[4,5]imidazo[2,1-b]oxazole-2,3'-bicyclo[2.2.2]octan]-1'-yl-10-ium) trihydroborate (0.60 g, 2 mmol) from example 5, step A in acetone (5 mL) was added 3 M HCl (1.3 mL, 4 mmol). The reaction mixture was stirred at RT for 30 min. and then neutralized with 1 N NaOH until the pH was ~8-9. The mixture was extracted with ethyl acetate. The organics were dried with MgSO₄, filtered, and the solvent was removed to yield deprotected racemic product. The racemic material was separated using a chiral column (Chiralcel OD 21×250 mm 10 u, inj. vol. 2000 uL, isocratic, start % B: 45, flow rate: 15 ml/min., collection time 2 to 20 min, solvent A: 0.1% diethylamine/heptane, solvent B: ethanol, wavelength: 220 nM)) to yield two enantiomers (enantiomer 1 and enantiomer 2). Enantiomer 2, second off the column, RT=10.8 min, (R)-6,7-dimethyl-3H-1'-azaspiro[benzo[4,5]imidazo[2,1-b]oxazole-2,3'-bicyclo[2.2.2]octane] (0.20 g, 0.7 mmol, 34.6% yield). $^1$H NMR (500 MHz, DMSO-$d_6$) δ 7.14 (s, 1H), 7.03 (s, 1H), 4.43 (d, J=9.6 Hz, 1H), 4.14 (d, J=9.6 Hz, 1H), 3.16 (s, 2H), 2.81 (s, 2H), 2.70 (d, J=8.1 Hz, 2H), 2.31-2.14 (m, 7H), 2.02-1.83 (m, 1H), 1.65 (br. s., 2H), 1.57-1.43 (m, 1H). MS (LC/MS) R.T.=2.02; $[M+1]^+$= 284.09. Optical Rotation=−37.49°. Enantiomer 1, first off the column, RT=6.75 min., (S)-6,7-dimethyl-3H-1'-azaspiro[benzo[4,5]imidazo[2,1-b]oxazole-2,3'-bicyclo[2.2.2]octane] (0.25 g, 0.873 mmol, 43.3% yield). $^1$H NMR (500 MHz, DMSO-$d_6$) δ 7.14 (s, 1H), 7.02 (s, 1H), 4.43 (d, J=9.5 Hz, 1H), 4.14 (d, J=9.5 Hz, 1H), 3.16 (s, 2H), 2.88-2.63 (m, 4H), 2.37-2.10 (m, 7H), 1.97-1.85 (m, 1H), 1.72-1.62 (m, 2H), 1.57-1.40 (m, 1H). MS (LC/MS) R.T.=2.13; $[M+1]^+$= 284.10. Optical Rotation=+36.66°.

EXAMPLE 6

(R)-7-Methoxy-3H-1'-azaspiro[benzo[4,5]imidazo[2,1-b]oxazole-2,3'-bicyclo [2.2.2]octane], (S)-7-methoxy-3H-1'-azaspiro[benzo[4,5]imidazo[2,1-b]oxazole-2,3'-bicyclo [2.2.2]octane], (R)-6-methoxy-3H-1'-azaspiro[benzo[4,5]imidazo[2,1-b]oxazole-2,3'-bicyclo [2.2.2]octane], and (S)-6-methoxy-3H-1'-azaspiro[benzo[4,5]imidazo[2,1-b]oxazole-2,3'-bicyclo [2.2.2]octane]

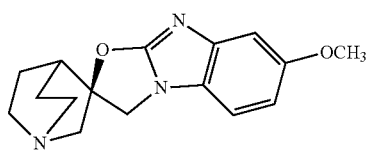
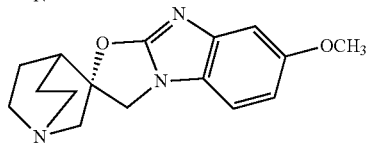
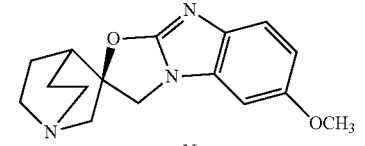
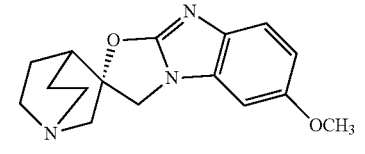

Step A: (7-Methoxy-3H-1'-azaspiro[benzo[4,5]imidazo[2,1-b]oxazole-2,3'-bicyclo[2.2.2]octan]-1'-yl-10-ium)trihydroborate, and (6-methoxy-3H-1'-azaspiro[benzo[4,5]imidazo[2,1-b]oxazole-2,3'-bicyclo [2.2.2]octan]-1'-yl-10-ium)trihydroborate

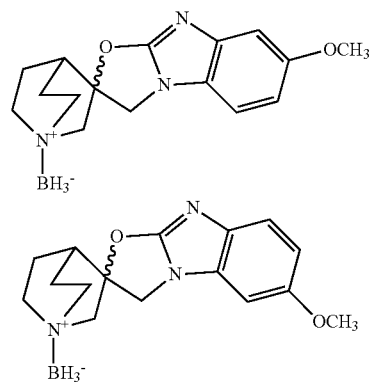

To 2-chloro-6-methoxy-1H-benzo[d]imidazole (0.55 g, 3.0 mmol) in THF (15 mL) was added n-butyllithium (1.2 mL, 3 mmol) dropwise at −78° C. After 45 minutes, a solution of racemic 1'-azaspiro[oxirane-2,3'-bicyclo[2.2.2]octan]-1'-yl-4-iumtrihydroborate (0.51 g, 3.3 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO₄, filtered and the solvent was removed to yield the crude product. The crude material was purified by chromatography (Biotage) to yield a mixture of racemic regioisomers, (6-methoxy-3H-1'-azaspiro[benzo[4,5]imidazo[2,1-b]oxazole-2,3'-bicyclo [2.2.2]octan]-1'-yl-10-ium)trihydroborate and (7-methoxy-3H-1'-azaspiro[benzo[4,5]imidazo[2,1-b]oxazole-2,3'-bicyclo[2.2.2]octan]-1'-yl-10-ium)trihydroborate (0.6 g, 2 mmol, 66.6% yield). The two regiosiomers were taken on to the next step.

Step B: (R)-7-Methoxy-3H-1'-azaspiro[benzo[4,5]imidazo[2,1-b]oxazole-2,3'-bicyclo[2.2.2]octane], (S)-7-methoxy-3H-1'-azaspiro[benzo[4,5]imidazo[2,1-b]oxazole-2,3'-bicyclo[2.2.2]octane], (R)-6-methoxy-3H-1'-azaspiro[benzo[4,5]imidazo[2,1-b]oxazole-2,3'-bicyclo[2.2.2]octane],and (S)-6-methoxy-3H-1'-azaspiro[benzo[4,5]imidazo[2,1-b]oxazole-2,3'-bicyclo[2.2.2]octane]

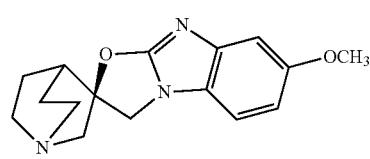
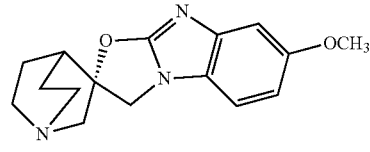

-continued

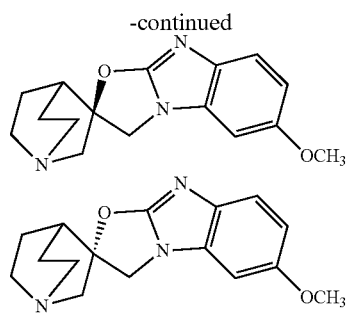

To the mixture of racemic regioisomers, (6-methoxy-3H-1'-azaspiro[benzo[4,5]imidazo[2,1-b]oxazole-2,3'-bicyclo[2.2.2]octan]-1'-yl-10-ium)trihydroborate and (7-methoxy-3H-1'-azaspiro[benzo[4,5]imidazo[2,1-b]oxazole-2,3'-bicyclo[2.2.2]octan]-1'-yl-10-ium)trihydroborate (0.21 g, 0.7 mmol) from example 6, step A, in acetone (5 mL) was added 3 M HCl (0.49 mL, 1.40 mmol). The reaction stirred for 30 minutes and then the reaction mixture was neutralized to a pH ~8-9 using 1 N NaOH. The reaction mixture was extracted with ethyl acetate, dried with MgSO$_4$, filtered and the solvent was removed to yield the product as a mixture of deprotected racemic 6 and 7-regioisomers. A chiral column (Chiralpak AD 21×250 mm 10 u, inj. vol. 2000 uL, isocratic, start % B: 45, flow rate: 15 ml/min., collection time 2 to 25 min, solvent A: 0.1% diethylamine/heptane, solvent B: ethanol, wavelength: 220 nM) was used to separate the material to yield three peaks. Peak 1 was one enantiomer of the 7-regioisomer and peak 3 was the 2nd enantiomer. Peak 2 was the 6-regioisomer as a racemic mixture. 1H NMR and X-ray studies concluded peak 1 was (S)-7-methoxy-3H-1'-azaspiro[benzo[4,5]imidazo[2,1-b]oxazole-2,3'-bicyclo[2.2.2]octane] (0.03 g, 0.10 mmol, 14.8% yield) as a white powder. $^1$H NMR (500 MHz, DMSO-d$_6$) δ 7.14 (d, J=8.5 Hz, 1H), 6.96 (d, J=2.3 Hz, 1H), 6.68 (dd, J=8.5, 2.4 Hz, 1H), 4.45 (d, J=9.6 Hz, 1H), 4.17 (d, J=9.5 Hz, 1H), 3.73 (s, 3H), 3.20-3.11 (m, 2H), 2.82 (t, J=7.8 Hz, 2H), 2.71 (t, J=7.8 Hz, 2H), 2.26-2.20 (m, 1H), 1.93 (d, J=7.0 Hz, 1H), 1.71-1.61 (m, 2H), 1.56-1.42 (m, 1H). MS (LC/MS) R.T.=1.61; [M+1]$^+$=286.09. Peak 3 was (R)-7-methoxy-3H-1'-azaspiro[benzo[4,5]imidazo[2,1-b]oxazole-2,3'-bicyclo[2.2.2]octane] (0.031 g, 0.11 mmol, 15% yield) as a white powder. $^1$H NMR (500 MHz, DMSO-d$_6$) δ 7.14 (d, J=8.5 Hz, 1H), 6.96 (d, J=2.3 Hz, 1H), 6.68 (dd, J=8.5, 2.4 Hz, 1H), 4.45 (d, J=9.5 Hz, 1H), 4.17 (d, J=9.5 Hz, 1H), 3.73 (s, 3H), 3.17 (s, 2H), 2.82 (s, 2H), 2.71 (s, 2H), 2.28-2.18 (m, 1H), 2.02-1.87 (m, 1H), 1.73-1.58 (m, 2H), 1.56-1.40 (m, 1H). MS (LC/MS) R.T.=1.62; [M+1]$^+$=286.09. Peak 2 was a mixture of (R)-6-methoxy-3H-1'-azaspiro[benzo[4,5]imidazo[2,1-b]oxazole-2,3'-bicyclo[2.2.2]octane] and (S)-6-methoxy-3H-1'-azaspiro[benzo[4,5]imidazo-[2,1-b]oxazole-2,3'-bicyclo[2.2.2]octane] (0.022 g, 0.077 mmol, 11% yield). $^1$H NMR (500 MHz, DMSO-d$_6$) δ 7.23 (d, J=8.5 Hz, 1H), 6.90 (d, J=2.6 Hz, 1H), 6.68 (dd, J=8.7, 2.6 Hz, 1H), 4.46 (d, J=9.6 Hz, 1H), 4.17 (d, J=9.6 Hz, 1H), 3.82-3.70 (m, 3H), 3.24-3.10 (m, 2H), 2.81 (t, J=7.9 Hz, 2H), 2.71 (t, J=7.6 Hz, 2H), 2.21 (d, J=2.6 Hz, 1H), 2.02-1.85 (m, 1H), 1.74-1.59 (m, 2H), 1.52 (d, J=11.1 Hz, 1H). MS (LC/MS) R.T.=1.81; [M+1]$^+$=286.09.

EXAMPLE 7

(R)-7-Methyl-3H-1'-azaspiro[benzo[4,5]imidazo[2,1-b]oxazole-2,3'-bicyclo[2.2.2]octane], (S)-7-methyl-3H-1'-azaspiro[benzo[4,5]imidazo[2,1-b]oxazole-2,3'-bicyclo[2.2.2]octane], (R)-6-methyl-3H-1'-azaspiro[benzo[4,5]imidazo[2,1-b]oxazole-2,3'-bicyclo[2.2.2]octane], and (S)-6-methyl-3H-1'-azaspiro[benzo[4,5]imidazo[2,1-b]oxazole-2,3'-bicyclo[2.2.2]octane]

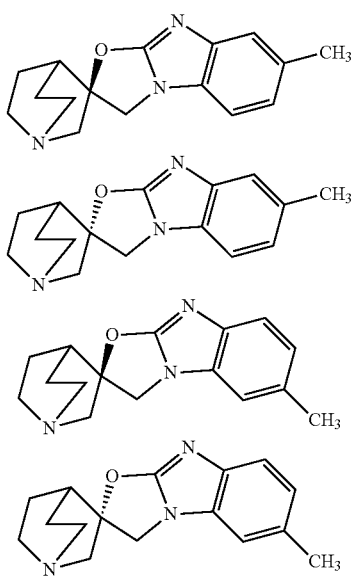

Step A: (7-Methyl-3H-1'-azaspiro[benzo[4,5]imidazo[2,1-b]oxazole-2,3'-bicyclo[2.2.2]octan]-1'-yl-10-ium)trihydroborate, and (6-methyl-3H-1'-azaspiro[benzo[4,5]imidazo[2,1-b]oxazole-2,3'-bicyclo[2.2.2]octan]-1'-yl-10-um)trihydroborate, and (6-methyl-3H-1'-azaspiro[benzo[4,5]imidazo[2,1-b]oxazole-2,3'-bicyclo[2.2.2]octan]-1'-yl-10-ium)trihydroborate

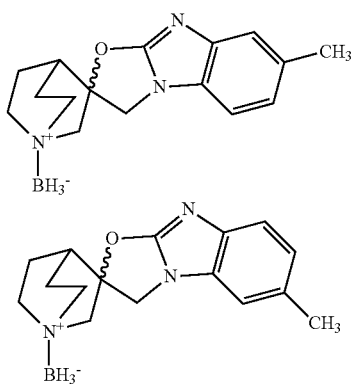

To 2-chloro-6-methyl-1H-benzo[d]imidazole (0.60 g, 3.6 mmol) in THF (15 mL) was added n-butyllithium (1.44 mL, 3.6 mmol) dropwise at −78° C. After 45 minutes, a solution of racemic (1'-azaspiro[oxirane-2,3'-bicyclo[2.2.2]octan]-1'-yl-4-ium)trihydroborate (0.61 g, 4 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with $MgSO_4$, filtered and the solvent was removed to yield the crude product. The crude material was purified by chromatography (Biotage) to yield a mixture of racemic regioisomers, (6-methyl-3H-1'-azaspiro[benzo[4,5]imidazo[2,1-b]oxazole-2,3'-bicyclo[2.2.2]octan]-1'-yl-10-ium)trihydroborate and ((1's,4's)-7-methyl-3H-1'-azaspiro[benzo[4,5]imidazo[2,1-b]oxazole-2,3'-bicyclo[2.2.2]octan]-1'-yl-10-ium)trihydroborate (0.6 g, 2 mmol, 56% yield) as white powder. The product was carried on to the next step.

Step B: (R)-7-Methyl-3H-1'-azaspiro[benzo[4,5]imidazo[2,1-b]oxazole-2,3'-bicyclo[2.2.2]octane], (S)-7-methyl-3H-1'-azaspiro[benzo[4,5]imidazo[2,1-b]oxazole-2,3'-bicyclo[2.2.2]octane], (R)-6-methyl-3H-1'-azaspiro[benzo[4,5]imidazo[2,1-b]oxazole-2,3'-bicyclo[2.2.2]octane], and (S)-6-methyl-3H-1'-azaspiro[benzo[4,5]imidazo[2,1-b]oxazole-2,3'-bicyclo[2.2.2]octane]

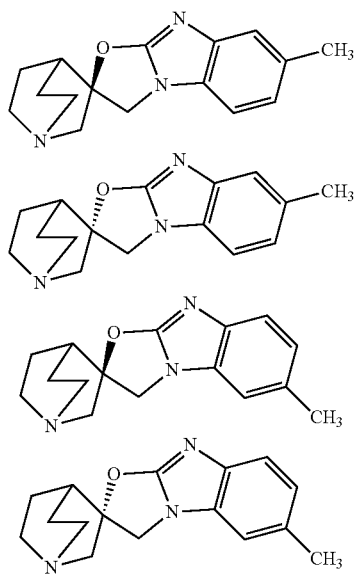

The mixture of racemic regioisomers, (6-methyl-3H-1'-azaspiro[benzo[4,5]imidazo[2,1-b]oxazole-2,3'-bicyclo[2.2.2]octan]-1'-yl-10-ium)trihydroborate and (7-methyl-3H-1'-azaspiro[benzo[4,5]imidazo[2,1-b]oxazole-2,3'-bicyclo[2.2.2]octan]-1'-yl-10-ium)trihydroborate (0.40 g, 1.4 mmol) from example 7, step A, in acetone (20 mL) was added 3 M hydrogen chloride (3.5 mL, 7.06 mmol) at room temperature. After 35 minutes, 1 N NaOH was added until the pH was ~8-9. The product was extracted with ethyl acetate, dried with $MgSO_4$, filtered and the solvent was removed to yield the deprotected racemic mixture of regioisomers. The racemic regioisomers were separated using a chiral column (Chiralpak AD 21×250 mm 10 u, inj. vol. 2000 uL, Isocratic, start % B: 35, flow rate 15 mL/min, stop time 31 min., solvent A: 0.1% diethylamine/heptane, solvent B: ethanol, wavelength 220 nm) to yield four peaks. The first two peaks, (S)-6-methyl-3H-1'-azaspiro[benzo[4,5]imidazo[2,1-b]oxazole-2,3'-bicyclo[2.2.2]octane] and (S)-7-methyl-3H-1'-azaspiro[benzo[4,5]imidazo[2,1-b]oxazole-2,3'-bicyclo[2.2.2]octane] did not separate, peak 3 and peak 4 were separable and the solvent was removed. Peak 4 was determined by $^1$H NMR to be (R)-6-methyl-3H-1'-azaspiro[benzo[4,5]imidazo[2,1-b]oxazole-2,3'-bicyclo[2.2.2]octane] (0.05 g, 0.18 mmol, 12.6% yield). $^1$H NMR (500 MHz, DMSO-$d_6$) δ 7.22 (d, J=8.1 Hz, 1H), 7.10-7.01 (m, 1H), 6.89 (dd, J=8.1, 1.1 Hz, 1H), 4.46 (d, J=9.6 Hz, 1H), 4.17 (d, J=9.5 Hz, 1H), 3.17 (s, 2H), 2.82 (t, J=7.8 Hz, 2H), 2.74-2.63 (m, 2H), 2.37 (s, 3H), 2.26-2.12 (m, 1H), 2.06-1.84 (m, 1H), 1.70-1.61 (m, 2H), 1.52 (d, J=11.1 Hz, 1H). MS (LC/MS) R.T.=1.85; [M+1]$^+$=270.22. Optical Rotation=−36.29°. Peak 3 was (R)-7-methyl-3H-1'-azaspiro[benzo[4,5]imidazo[2,1-b]oxazole-2,3'-bicyclo[2.2.2]octane] (0.05 g, 0.18 mmol, 12.6% yield). $^1$H NMR (500 MHz, DMSO-$d_6$) δ 7.21-7.08 (m, 2H), 6.89 (br. s., 1H), 4.46 (d, J=6.4 Hz, 1H), 4.18 (d, J=7.3 Hz, 1H), 3.18 (br. s., 2H), 2.81 (br. s., 2H), 2.71 (br. s., 2H), 2.35 (br. s., 3H), 2.22 (br. s., 1H), 1.94 (br. s., 1H), 1.65 (br. s., 2H), 1.53 (br. s., 1H). MS (LC/MS) R.T.=1.81; [M+1]$^+$=270.21. Optical Rotation=−51.24°.

EXAMPLE 8

(R)-7-(Trifluoromethyl)-3H-1'-azaspiro[benzo[4,5]imidazo[2,1-b]oxazole-2,3'-bicyclo[2.2.2]octane], (S)-7-(trifluoromethyl)-3H-1'-azaspiro[benzo[4,5]imidazo[2,1-b]oxazole-2,3'-bicyclo[2.2.2]octane], (R)-6-(trifluromethyl)-3H-1'-azaspiro[benzo[4,5]imidazo[2,1-b]oxazole-2,3'-bicyclo[2.2.2]octane], and (S)-6-(trifluoromethyl)-3H-1'-azaspiro[benzo[4,5]imidazo[2,1-b]oxazole-2,3'-bicyclo[2.2.2]octane]

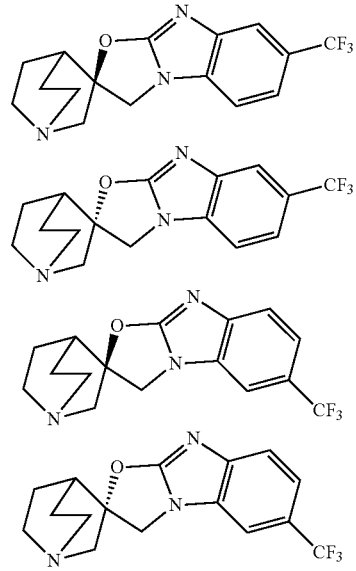

Step A: (7-(Trifluoromethyl)-3H-1'-azaspiro[benzo[4,5]imidazo[2,1-b]oxazole-2,3'-bicyclo[2.2.2]octan]-1'-yl-10-ium)trihydroborate and -6-(trifluoromethyl)-3H-1'-azaspiro[benzo[4,5]imidazo[2,1-b]oxazole-2,3'-bicyclo[2.2.2]octan]-1'-yl-10-ium)trihydroborate

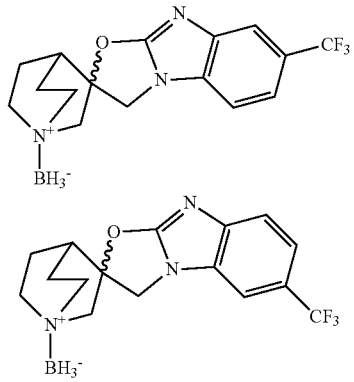

To 2-chloro-6-(trifluoromethyl)-1H-benzo[d]imidazole (0.50 g, 2.3 mmol) in THF (35 mL) was added n-butyllithium (0.91 mL, 2.3 mmol) dropwise at −78° C. After 45 minutes, a solution of racemic (1'-azaspiro[oxirane-2,3'-bicyclo[2.2.2]octan]-1'-yl-4-ium)trihydroborate (0.38 g, 2.5 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO₄, filtered and the solvent was removed to yield the crude product. The crude material was purified by chromatography (Biotage) to yield a mixture of racemic regioisomers, (7-(trifluoromethyl)-3H-1'-azaspiro[benzo[4,5]imidazo[2,1-b]oxazole-2,3'-bicyclo[2.2.2]octan]-1'-yl-10-ium)trihydroborate and ((1's,4's)-6-(trifluoromethyl)-3H-1'-azaspiro[benzo[4,5]imidazo[2,1-b]oxazole-2,3'-bicyclo[2.2.2]octan]-1'-yl-10-ium)trihydroborate (0.52 g, 1.5 mmol, 68% yield). The product was carried on to the next step.

Step B: (R)-7-(Trifluoromethyl)-3H-1'-azaspiro[benzo[4,5]imidazo[2,1-b]oxazole-2,3'-bicyclo[2.2.2]octane], (S)-7-(trifluoromethyl)-3H-1'-azaspiro[benzo[4,5]imidazo[2,1-b]oxazole-2,3'-bicyclo[2.2.2]octane], (R)-6-(trifluoromethyl)-3H-1'-azaspiro[benzo[4,5]imidazo[2,1-b]oxazole-2,3'-bicyclo[2.2.2]octane], and (S)-6-(trifluoromethyl)-3H-1'-azaspiro[benzo[4,5]imidazo[2,1-b]oxazole-2,3'-bicyclo[2.2.2]octane]

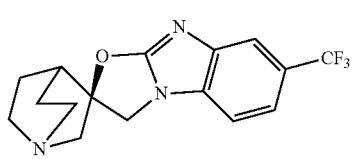

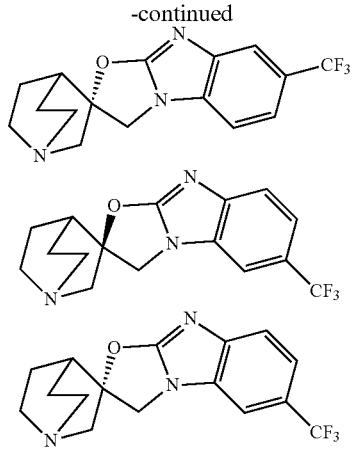

To the racemic regioisomers (0.40 g, 1.2 mmol) from example 8, step A, in acetone (20 mL) was added 3 M hydrogen chloride (3 mL, 5.9 mmol) at room temperature. After 35 minutes, 1 N NaOH was added until the pH ~8-9. The product was extracted with ethyl acetate, dried with MgSO₄, filtered and the solvent was removed to yield the deprotected racemic mixture of regioisomers. The racemic material was separated using a chiral column (Chiralpak AD 21×250 mm 10 u, inj. vol. 2000 uL, Isocratic, start % B: 35, flow rate 15 mL/min, stop time 31 min., solvent A: 0.1% diethylamine/heptane, solvent B: ethanol, UV monitored 220 nm) to yield four peaks. The first two peaks, (S)-7-(trifluoromethyl)-3H-1'-azaspiro[benzo[4,5]imidazo[2,1-b]oxazole-2,3'-bicyclo[2.2.2]octane] and (S)-6-(trifluoromethyl)-3H-1'-azaspiro[benzo[4,5]imidazo[2,1-b]oxazole-2,3'-bicyclo[2.2.2]octane] did not initially separate and were separated after peak 3 and peak 4 were obtained. Peak 3 and peak 4 were separable and the solvent was removed. Peak 4 was determined by HNMR and X-ray to be (R)-7-(trifluoromethyl)-3H-1'-azaspiro[benzo[4,5]imidazo[2,1-b]oxazole-2,3'-bicyclo[2.2.2]octane] (0.043 g, 0.13 mmol, 11% yield). ¹H NMR (400 MHz, DMSO-d₆) δ 7.70 (s, 1H), 7.46 (q, J=8.3 Hz, 2H), 4.61 (d, J=9.8 Hz, 1H), 4.31 (d, J=10.0 Hz, 1H), 3.22 (d, J=3.0 Hz, 2H), 2.83 (t, J=7.7 Hz, 2H), 2.72 (t, J=7.7 Hz, 2H), 2.28 (br. s., 1H), 1.94 (br. s., 1H), 1.67 (t, J=7.5 Hz, 2H), 1.59-1.41 (m, 1H). MS (LC/MS) R.T.=2.66; [M+1]⁺=324.01. Optical Rotation=−32.51°. Peak 3 was (R)-6-(trifluoromethyl)-3H-1'-azaspiro[benzo[4,5]imidazo[2,1-b]oxazole-2,3'-bicyclo[2.2.2]octane] (0.04 g, 0.12 mmol, 10% yield). ¹H NMR (500 MHz, DMSO-d₆) δ 7.70 (s, 1H), 7.53 (d, J=8.2 Hz, 1H), 7.42 (s, 1H), 4.61 (d, J=9.8 Hz, 1H), 4.28 (d, J=9.9 Hz, 1H), 3.21 (d, J=11.0 Hz, 2H), 2.83 (t, J=7.6 Hz, 2H), 2.76-2.67 (m, 2H), 2.27 (br. s., 1H), 2.02-1.89 (m, 1H), 1.76-1.60 (m, 2H), 1.59-1.45 (m, 1H). MS (LC/MS) R.T.=2.66; [M+1]⁺=324.02. Optical Rotation=−41.23°. The mixture of peaks 1 and 2 was then separated using a Chiralpak AD-H analytical column, 4.6× 250 mm, 5 μm, mobile phase: 15% methanol with 0.1% diethylamine in CO₂, injection: 5 uL of ~1 mg/mL solution in methanol, temp: 35° C., pressure: 150 bar, flow rate: 2.0 mL/min, UV monitored 220 nm. Peak 1 (Retention time=6.9 min.) was obtained and the solvent was removed to yield a white powder. Peak 1 was determined to be (S)-6-(trifluoromethyl)-3H-1'azaspiro[benzo[4,5]imidazo[2,1-b]oxazole-2,3'-bicyclo[2.2.2]octane] (0.043 g, 0.13 mmol, 11% yield). ¹H NMR (500 MHz, DMSO-d₆) δ 7.70 (s, 1H), 7.53 (d, J=8.4 Hz, 1H), 7.41 (d, J=8.4 Hz, 1H), 4.61 (d, J=9.9 Hz, 1H), 4.28 (d, J=9.9 Hz, 1H), 3.26-3.11 (m, 2H), 2.83 (t, J=7.9 Hz, 2H), 2.72 (t, J=7.7 Hz, 2H), 2.27 (br. s., 1H), 2.04-1.88 (m, 1H), 1.75-1.59 (m, 2H), 1.56-1.44 (m, 1H). MS (LC/MS) R.T.=2.60; [M+1]⁺=324.18. Optical Rotation=+31.71°. Peak 2 (Retention time=10.77 min.) was obtained and the solvent was removed to yield a white powder. Peak 2 was determined to be (S)-7-(trifluoromethyl)-3H-1'-azaspiro[benzo[4,5]imidazo[2,1-b]oxazole-2,3'-bicyclo[2.2.2]octane] (0.04 g, 0.12 mmol, 10% yield). $^1$H NMR (500 MHz, DMSO-d$_6$) δ 7.69 (s, 1H), 7.56-7.35 (m, 2H), 4.60 (d, J=9.8 Hz, 1H), 4.30 (d, J=9.9 Hz, 1H), 3.26-3.13 (m, 2H), 2.83 (t, J=7.8 Hz, 2H), 2.72 (t, J=7.7 Hz, 2H), 2.31-2.22 (m, 1H), 2.00-1.83 (m, 1H), 1.73-1.61 (m, 2H), 1.60-1.44 (m, 1H). MS (LC/MS) R.T.=2.61; [M+1]$^+$=324.18. Optical Rotation=+29.51°.

EXAMPLE 9

(R)-8-Chloro-3H-1'-azaspiro[benzo[4,5]imidazo[2,1-b]oxazole-2,3'-bicyclo[2.2.2]octane], (S)-8-chloro-3H-1'-azaspiro[benzo[4,5]imidazo[2,1-b]oxazole-2,3'-bicyclo[2.2.2]octane], (R)-5-chloro-3H-1'-azaspiro[benzo[4,5]imidazo[2,1-b]oxazole-2,3'-bicyclo[2.2.2]octane], and (S)-5-chloro-3H-1'-azaspiro[benzo[4,5]imidazo[2,1-b]oxazole-2,3'-bicyclo[2.2.2]octane]

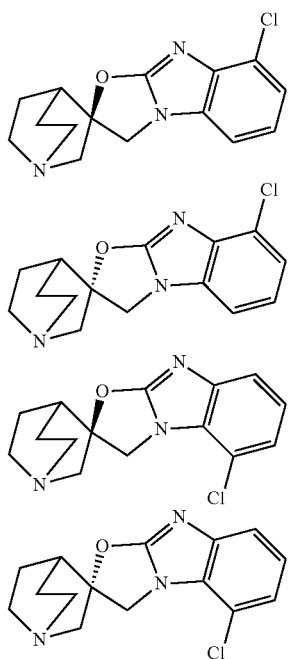

Step A: (8-Chloro-3H-1'-azaspiro[benzo[4,5]imidazo[2,1-b]oxazole-2,3'-bicyclo[2.2.2]octan]-1'-yl-8-ium)trihydroborate and (5-chloro-3H-1'-azaspiro[benzo[4,5]imidazo[2,1-b]oxazole-2,3'-bicyclo[2.2.2]octan]-1'-yl-8-ium)trihydroborate

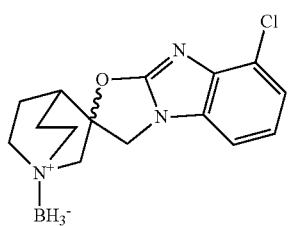

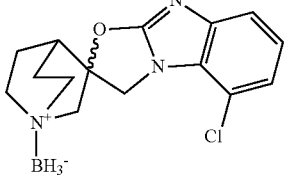

To 2,7-dichloro-1H-benzo[d]imidazole (0.51 g, 2.7 mmol) in THF (15 mL) was added n-butyllithium (1.1 mL, 2.7 mmol) dropwise at −78° C. After 45 minutes, a solution of racemic (1'-azaspiro[oxirane-2,3'-bicyclo[2.2.2]octan]-1'-yl-4-ium)trihydroborate (0.46 g, 3 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield the separated regioisomers. The solvent was removed from both compounds to yield racemic (5-chloro-3H-1'-azaspiro[benzo[4,5]imidazo[2,1-b]oxazole-2,3'-bicyclo[2.2.2]octan]-1'-yl-10-ium)trihydroborate (0.28 g, 0.87 mmol, 32% yield) (P1) and racemic (8-chloro-3H-1'-azaspiro[benzo[4,5]imidazo[2,1-b]oxazole-2,3'-bicyclo[2.2.2]octan]-1'-yl-10-ium)trihydroborate (0.31 g, 0.95 mmol, 35% yield) (P2) as powders. The products were carried on to the next step.

(5-Chloro-3H-1'-azaspiro[benzo[4,5]imidazo[2,1-b]oxazole-2,3'-bicyclo[2.2.2]octan]-1'-yl-10-ium)trihydroborate (P1): $^1$H NMR (500 MHz, DMSO-d$_6$) δ 7.36 (dd, J=7.8, 1.1 Hz, 1H), 7.18-7.03 (m, 2H), 4.67 (d, J=9.9 Hz, 1H), 4.57 (d, J=9.9 Hz, 1H), 3.48 (dd, J=15.3, 2.4 Hz, 1H), 3.36-3.31 (m, 3H), 3.04 (d, J=2.4 Hz, 1H), 2.98-2.86 (m, 3H), 2.48-2.39 (m, 1H), 2.07 (br. s., 1H), 1.93-1.75 (m, 3H), 1.66-1.24 (m, 3H).

(8-Chloro-3H-1'-azaspiro[benzo[4,5]imidazo[2,1-b]oxazole-2,3'-bicyclo[2.2.2]octan]-1'-yl-10-ium)trihydroborate (P2): $^1$H NMR (500 MHz, DMSO-d$_6$) δ 7.27 (dd, J=7.9, 1.0 Hz, 1H), 7.21-7.14 (m, 1H), 7.13-7.03 (m, 1H), 4.57 (d, J=9.9 Hz, 1H), 4.33 (d, J=9.9 Hz, 1H), 3.52-3.41 (m, 1H), 3.36 (d, J=1.7 Hz, 1H), 3.10-3.00 (m, 1H), 2.98-2.82 (m, 3H), 2.45 (d, J=1.8 Hz, 1H), 2.18-2.01 (m, 1H), 1.92-1.74 (m, 3H), 1.46 (br. s., 3H)

Step B: (R)-8-Chloro-3H-1'-azaspiro[benzo[4,5]imidazo[2,1-b]oxazole-2,3'-bicyclo[2.2.2]octane] and (S)-8-chloro-3H-1'-azaspiro[benzo[4,5]imidazo[2,1-b]oxazole-2,3'-bicyclo[2.2.2]octane]

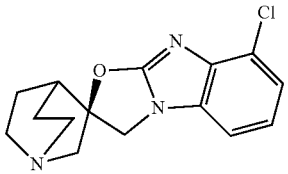

-continued

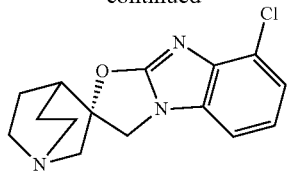

To racemic (8-chloro-3H-1'-azaspiro[benzo[4,5]imidazo[2,1-b]oxazole-2,3'-bicyclo[2.2.2]octan]-1'-yl-10-ium)trihydroborate (0.30 g, 1 mmol) from example 9, step A, in acetone (5 mL) was added 3 M HCl (0.7 mL, 2 mmol) at room temperature. After 35 minutes, 1 N NaOH was added until the pH ~8-9. The product was extracted with ethyl acetate, dried with MgSO$_4$, filtered and the solvent was removed to yield the deprotected racemic regiosiomer (P2). The racemic material was separated into its enantiomers, P2E1 and P2E2, using Chiralcel OD 21×250 mm 10 u, inj. vol. 2000 uL, isocratic, start % B: 45, flow rate: 15 mL/min, run time: 18 min., solvent A: 0.1% diethylamine/heptane, solvent B: ethanol, wavelength: 220. For P2E1 (enantiomer 1), the RT=6.0 min. and for P2E2 (enantiomer 2), the RT=9.16 min. The solvent was removed to yield the two enantiomers. P2E1 (enantiomer 1) (S)-8-chloro-3H-1'-azaspiro[benzo[4,5]imidazo[2,1-b]oxazole-2,3'-bicyclo[2.2.2]octane] (0.1 g, 0.32 mmol, 32% yield). P2E1: $^1$H NMR (500 MHz, DMSO-d$_6$) δ 7.26 (dd, J=7.8, 0.9 Hz, 1H), 7.15 (dd, J=8.0, 1.0 Hz, 1H), 7.11-7.02 (m, 1H), 4.56 (d, J=9.6 Hz, 1H), 4.26 (d, J=9.6 Hz, 1H), 3.25-3.13 (m, 2H), 2.88-2.76 (m, 2H), 2.71 (t, J=7.7 Hz, 2H), 2.31-2.22 (m, 1H), 1.94 (d, J=4.6 Hz, 1H), 1.66 (dt, J=7.4, 3.4 Hz, 2H), 1.58-1.39 (m, 1H). MS (LC/MS) R.T.=2.27; [M+1]$^+$=290.03. Optical Rotation=+32.86°. P2E2 (enantiomer 2) (R)-8-chloro-3H-1'-azaspiro[benzo[4,5]imidazo[2,1-b]oxazole-2,3'-bicyclo[2.2.2]octane] (0.11 g, 0.35 mmol, 35% yield). P2E2: $^1$H NMR (500 MHz, DMSO-d$_6$) δ 7.26 (dd, J=7.9, 1.0 Hz, 1H), 7.20-7.13 (m, 1H), 7.13-7.01 (m, 1H), 4.56 (d, J=9.6 Hz, 1H), 4.26 (d, J=9.6 Hz, 1H), 3.24-3.14 (m, 2H), 2.82 (t, J=7.8 Hz, 2H), 2.71 (t, J=7.8 Hz, 2H), 2.31-2.22 (m, 1H), 1.94 (d, J=4.9 Hz, 1H), 1.73-1.58 (m, 2H), 1.58-1.45 (m, 1H). MS (LC/MS) R.T.=2.26; [M+1]$^+$=290.03. Optical Rotation=−26.09°.

Step B: (R)-5-Chloro-3H-1'-azaspiro[benzo[4,5]imidazo[2,1-b]oxazole-2,3'-bicyclo[2.2.2]octane] and (S)-5-chloro-3H-1'azaspiro[benzo[4,5]imidazo[2,1-b]oxazole-2,3'-bicyclo[2.2.2]octane]

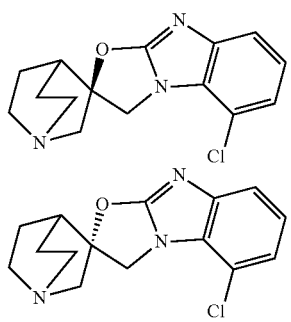

To racemic (5-chloro-3H-1'-azaspiro[benzo[4,5]imidazo[2,1-b]oxazole-2,3'-bicyclo[2.2.2]octan]-1'-yl-10-ium)trihydroborate (0.25 g, 0.8 mmol) from example 9, step A, in acetone (5 mL) was added 3 M HCl (0.55 mL, 1.6 mmol) at room temperature. After 35 minutes, 1 N NaOH was added until the pH ~8-9. The product was extracted with ethyl acetate, dried with MgSO$_4$, filtered and the solvent was removed to yield the deprotected racemic regiosiomer (P1). The racemic material was separated into its' enantiomers, P1E1 and P1E2, using Chiralcel OJ 21×250 mm 10 u, inj. vol. 2000 uL, isocratic, start % B: 30, flow rate: 15 mL/min, run time: 20 min., solvent A: 0.1% diethylamine/heptane, solvent B: ethanol, wavelength: 220. For P1E1 (enantiomer 1), the RT=7.7 min. and for P1E2 (enantiomer 2), the RT=8.6 min. The solvent was removed to yield the two enantiomers. Enantiomer 1 (P1E1), (R)-5-chloro-3H-1'-azaspiro[benzo[4,5]imidazo[2,1-b]oxazole-2,3'-bicyclo[2.2.2]octane] (0.05 g, 0.17 mmol, 20% yield). $^1$H NMR (500 MHz, DMSO-d$_6$) δ 7.33 (dd, J=7.7, 1.1 Hz, 1H), 7.17-6.99 (m, 2H), 4.66 (d, J=9.6 Hz, 1H), 4.47 (d, J=9.6 Hz, 1H), 3.26-3.13 (m, 2H), 2.82 (t, J=7.9 Hz, 2H), 2.76-2.63 (m, 2H), 2.35-2.24 (m, 1H), 2.05-1.86 (m, 1H), 1.79-1.59 (m, 2H), 1.58-1.42 (m, 1H). MS (LC/MS) R.T.=2.33; [M+1]$^+$=290.03. Optical Rotation=−31.57°. Enantiomer 2 (P1E2), (S)-5-chloro-3H-1'-azaspiro[benzo[4,5]imidazo[2,1-b]oxazole-2,3'-bicyclo[2.2.2]octane] (0.055 g, 0.18 mmol, 22% yield). $^1$H NMR (500 MHz, DMSO-d$_6$) δ 7.33 (dd, J=7.7, 1.1 Hz, 1H), 7.17-7.00 (m, 2H), 4.66 (d, J=9.6 Hz, 1H), 4.47 (d, J=9.6 Hz, 1H), 3.27-3.12 (m, 2H), 2.82 (t, J=7.7 Hz, 2H), 2.77-2.62 (m, 2H), 2.36-2.22 (m, 1H), 1.93 (td, J=6.8, 2.9 Hz, 1H), 1.74-1.60 (m, 2H), 1.59-1.37 (m, 1H). MS (LC/MS) R.T.=2.33; [M+1]$^+$=290.03. Optical Rotation=+32.63°.

EXAMPLE 10

(R)-8-Methyl-3H-1'-azaspiro[benzo[4,5]imidazo[2,1-b]oxazole-2,3'-bicyclo[2.2.2]octane] and (S)-8-methyl-3H-1'-azaspiro[benzo[4,5]imidazo[2,1-b]oxazole-2,3'-bicyclo[2.2.2]octane]

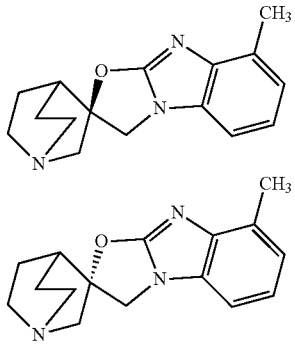

Step A: 2-Chloro-4-methyl-1H-benzo[d]imidazole

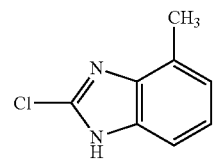

To 4-methyl-1H-benzo[d]imidazol-2(3H)-one (1.5 g, 10 mmol) was added POCl$_3$ (19 ml, 200 mmol) and the reaction mixture was heated to 135° C. for 3 hours. The reaction was then cooled to room temperature and the excess POCl₃ was removed in vacuo. The solid residue was diluted carefully with water and then slowly neutralized with saturated NaHCO₃ until the pH was ~7-8. The mixture was extracted with ethyl acetate (2×150 mL) and the organics extracts were combined. The organics were dried with MgSO₄, filtered, and the solvent was removed to yield the crude residue. The crude material was purified by chromatography (Biotage) to yield 2-chloro-7-methyl-1H-benzo[d]imidazole (1.1 g, 6.3 mmol, 62% yield) as a slightly yellow powder. MS (LC/MS) R.T.=2.61; [M+]⁺=166.93

Step B: (8-Methyl-3H-1'-azaspiro[benzo[4,5]imidazo[2,1-b]oxazole-2,3'-bicyclo[2.2.2]octan]-1'-yl-8-ium)trihydroborate

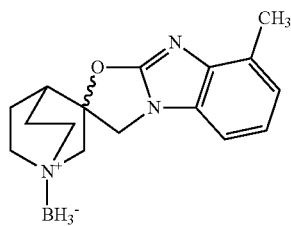

To 2-chloro-7-methyl-1H-benzo[d]imidazole (0.65 g, 3.9 mmol) from example 10, step A, in THF (35 mL) was added n-butyllithium (1.6 mL, 3.9 mmol) dropwise at −78° C. After 45 minutes, a solution of racemic (1'-azaspiro[oxirane-2,3'-bicyclo[2.2.2]octan]-1'-yl-4-ium)trihydroborate (0.66 g, 4.29 mmol) from the reference example, in THF (10 mL) was added dropwise at −78° C. The cooling bath ws removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO₄, filtered and the solvent was removed to yield the crude product. The crude material was purified by chromatography (Biotage) to yield racemic (8-methyl-3H-1'-azaspiro[benzo[4,5]imidazo[2,1-b]oxazole-2,3'-bicyclo[2.2.2]octan]-1'-yl-10-ium)trihydroborate (0.40 g, 1.4 mmol, 52%). The 5-methyl regioisomer product was not observed. MS (LC/MS) R.T.=1.90; [M+1-BH₃]⁺=270.07.

Step C: (R)-8-Methyl-3H-1'-azaspiro[benzo[4,5]imidazo[2,1-b]oxazole-2,3'-bicyclo[2.2.2]octane] and (S)-8-methyl-3H-1'-azaspiro[benzo[4,5]imidazo[2,1-b]oxazole-2,3'-bicyclo[2.2.2]octane]

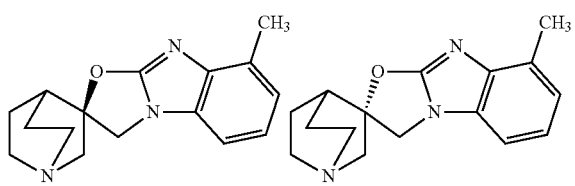

To racemic (8-methyl-3H-1'-azaspiro[benzo [4,5]imidazo[2,1-b]oxazole-2,3'-bicyclo[2.2.2]octan]-1'-yl-10-ium)trihydroborate (0.40 g, 1.4 mmol) from example 10, step B, in acetone (20 mL) was added 3 M hydrogen chloride (3.5 mL, 7.1 mmol) at room temperature. After 35 minutes, 1 N NaOH was added until the pH was ~8-9. The product was extracted with ethyl acetate, dried with MgSO₄, filtered and the solvent was removed to yield the deprotected racemic product. The racemic material was separated using a chiral column (Chiralcel OD 21×250 mm 10 u, inj. vol. 2000 uL, Isocratic, start % B: 25, flow rate 15 mL/min, stop time 25 min., solvent A: 0.1% diethylamine/heptane, solvent B: ethanol, wavelength 220 nm) to yield two peaks. Peak 1 (RT=7.7 min) and peak 2 (RT=13.1 min.) were separable and the solvent was removed. Peak 1 was determined by ¹H NMR to be (S)-8-methyl-3H-1'-azaspiro[benzo[4,5]imidazo[2,1-b]oxazole-2,3'-bicyclo[2.2.2]octane] (0.09 g, 0.33 mmol, 23% yield). ¹H NMR (500 MHz, DMSO-d₆) δ 7.07 (d, J=7.3 Hz, 1H), 6.99-6.86 (m, 2H), 4.48 (d, J=9.6 Hz, 1H), 4.19 (d, J=9.6 Hz, 1H), 3.18 (s, 2H), 2.88-2.76 (m, 2H), 2.74-2.64 (m, 2H), 2.39 (s, 3H), 2.28-2.15 (m, 1H), 2.04-1.87 (m, 1H), 1.71-1.62 (m, 2H), 1.57-1.41 (m, 1H). MS (LC/MS) R.T.=1.85; [M+1]⁺=270.20. Optical Rotation=+32.97°. Peak 2 was (R)-8-methyl-3H-1'-azaspiro[benzo[4,5]imidazo[2,1-b]oxazole-2,3'-bicyclo[2.2.2]octane] (0.07 g, 0.26 mmol, 18% yield). ¹H NMR (500 MHz, DMSO-d₆) δ 7.07 (d, J=7.6 Hz, 1H), 7.00-6.86 (m, 2H), 4.48 (d, J=9.6 Hz, 1H), 4.19 (d, J=9.6 Hz, 1H), 3.18 (s, 2H), 2.89-2.77 (m, 2H), 2.75-2.65 (m, 2H), 2.39 (s, 3H), 2.27-2.16 (m, 1H), 1.95 (d, J=5.2 Hz, 1H), 1.66 (t, J=5.3 Hz, 2H), 1.57-1.44 (m, 1H). MS (LC/MS) R.T.=1.75; [M+1]⁺=270.19. Optical Rotation=−34.95°.

EXAMPLE 11

(R)-8-(Trifluoromethyl)-3H-1'-azaspiro[benzo[4,5]imidazo[2,1-b]oxazole-2,3'-bicyclo[2.2.2]octane] and (S)-8-(trifluoromethyl)1-3H-1'-azaspiro[benzo[4,5]imidazo[2,1-b]oxazole-2,3'-bicyclo[2.2.2]octane]

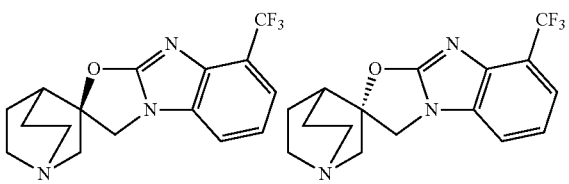

Step A: 4-(Trifluoromethyl)-1H-benzo[d]imidazol-2(3H)-one

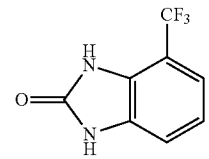 [SMILES: O=c1[nH]c2cccc(C(F)(F)F)c2[nH]1]

To a solution of 3-(trifluoromethyl)benzene-1,2-diamine (2 g, 11 mmol) in anhydrous THF (60 mL) was added CDI (3.7 g, 23 mmol). The reaction mixture was stirred at room temperature overnight. The solvent was removed under reduced pressure and the residue chromatographed (Biotage) to yield a cream colored powder, 4-(trifluoromethyl)-1H-benzo[d]imidazol-2(3H)-one (1.8 g, 8.9 mmol, 78% yield), which was carried on to the next step without any further purification. ¹H NMR (500 MHz, DMSO-d₆) δ 11.40-10.83 (m, 2H), 7.27-7.01 (m, 3H). MS (LC/MS) R.T.=4.88; [M+1]⁺=203.03.

Step B: 2-Chloro-4-(trifluoromethyl)-1H-benzo[d]imidazole

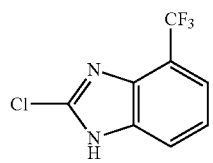 [SMILES: FC(F)(F)c1cccc2[nH]c(Cl)nc12]

To 4-(trifluoromethyl)-1H-benzo[d]imidazol-2(3H)-one (1.7 g, 8.4 mmol) from example 11, step A, was added POCl₃ (7.8 ml, 84 mmol). The reaction mixture was stirred at 120° C. for 2 hours and then cooled to room temperature. The mixture was stirred overnight and the excess POCl₃ was removed in vacuo. The remaining crude material was cooled in an ice bath and ethyl acetate was added with very small amounts of water. The resulting mixture was then slowly poured into an ice cooled flask containing water. The flask was allowed to warm to room temperature and the mixture was then neutralized with sat'd NaHCO₃. The organics were separated, dried with MgSO₄, filtered and the solvent was removed to yield a brown powder. The crude material was purified by chromatography (Biotage) to yield 2-chloro-4-(trifluoromethyl)-1H-benzo[d]imidazole (1.1 g, 5 mmol, 59% yield) as a powder.

Step C: (R)-8-Trifluoromethyl)-3H-1'-azaspiro[benzo[4,5]imidazo[2,1-b]oxazole-2,3'-bicyclo[2.2.2]octane] and (S)-8-(trifluoromethyl)-3H-1'-azaspiro[benzo[4,5]imidazo[2,1-b]oxazole-2,3'-bicyclo[2.2.2]octane]

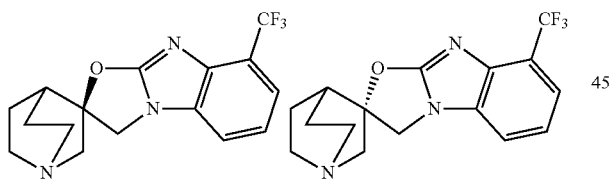

To 2-chloro-4-(trifluoromethyl)-1H-benzo[d]imidazole (0.53 g, 2.4 mmol) from example 11, step B, in THF (30 mL) was added dropwise n-butyllithium (1 mL, 2.4 mmol) at −78° C. The reaction mixture was stirred for 15 min. and then racemic (1'-azaspiro[oxirane-2,3'-bicyclo[2.2.2]octan]-1'-yl-4-ium)trihydroborate (0.44 g, 2.9 mmol) from the reference example, was added to the reaction. The reaction was stirred for an additional 10 min. at −78° C. and then was allowed to warm to room temperature. After 30 min., the reaction was heated to 70° C. for 2 hours and then cooled to room temperature. The reaction was quenched with water and the product was extracted with ethyl acetate (100 mL). The organics were dried with MgSO₄, filtered and the solvent was removed to yield the crude product. The crude material was purified by chromatography (Biotage) and the solvent was removed to yield racemic (8-(trifluoromethyl)-3H-1'-azaspiro[benzo[4,5]imidazo[2,1-b]oxazole-2,3'-bicyclo[2.2.2]octan]-1'-yl-10-ium)trihydroborate. (The 5-methyl regioisomer product was not observed.) Racemic (8-(trifluoromethyl)-3H-1'-azaspiro[benzo[4,5]imidazo[2,1-b)]oxazole-2,3'-bicyclo[2.2.2]octan]-1'-yl-10-ium)trihydroborate was dissolved in acetone (20 mL) and 3 M hydrogen chloride (3 mL, 5.9 mmol) was added at room temperature. After 35 minutes, 1 N NaOH was added until the pH was ~8-9. The product was extracted with ethyl acetate, dried with MgSO₄, filtered and the solvent was removed to yield the deprotected racemic product. The racemic material was separated using a chiral column (Chiralpak AD 21×250 mm 10 u, inj. vol. 2000 uL, Isocratic, start % B: 15, flow rate 15 mL/min, stop time 23 min., solvent A: 0.1% diethylamine/heptane, solvnet B: ethanol, wavelength 220 nm) to yield two peaks. The solvent was removed for both peaks and peak 1 was determined by NMR to be (S)-8-(trifluoromethyl)-3H-1'-azaspiro[benzo[4,5]imidazo[2,1-b]oxazole-2,3'-bicyclo[2.2.2]octane] (0.17 g, 0.5 mmol, 21% yield). ¹H NMR (500 MHz, DMSO-d₆) δ 7.56 (d, J=7.8 Hz, 1H), 7.40 (d, J=7.8 Hz, 1H), 7.29-7.16 (m, 1H), 4.59 (d, J=9.8 Hz, 1H), 4.29 (d, J=9.8 Hz, 1H), 3.26-3.14 (m, 2H), 2.88-2.77 (m, 2H), 2.72 (t, J=7.8 Hz, 2H), 2.32-2.23 (m, 1H), 2.03-1.88 (m, 1H), 1.77-1.61 (m, 2H), 1.58-1.38 (m, 1H). Optical Rotation=+31.10°. Peak 2 was (R)-8-(trifluoromethyl)-3H-1'-azaspiro [benzo[4,5]imidazo [2,1-b]oxazole-2,3'-bicyclo [2.2.2]octane] (0.14 g, 0.42 mmol, 17% yield). ¹H NMR (500 MHz, DMSO-d₆) δ 7.56 (d, J=7.8 Hz, 1H), 7.40 (d, J=7.8 Hz, 1H), 7.22 (t, J=7.9 Hz, 1H), 4.59 (d, J=9.8 Hz, 1H), 4.29 (d, J=9.8 Hz, 1H), 3.26-3.13 (m, 2H), 2.90-2.77 (m, 2H), 2.73-2.62 (m, 2H), 2.29 (d, J=2.7 Hz, 1H), 2.02-1.88 (m, 1H), 1.76-1.60 (m, 2H), 1.57-1.43 (m, 1H). Optical Rotation=−34.39°.

EXAMPLE 12

(R)-8-(4-Methoxyphenyl))-3H-1'-azaspiro[benzo[4,5]imidazo[2,1-b]oxazole-2,3'-bicyclo[2.2.2]octane], and (S)-8-(4-methoxyphenyl))-3H-1'-azaspiro[benzo[4,5]imidazo[2,1-b]oxazole-2,3'-bicyclo[2.2.2]octane]

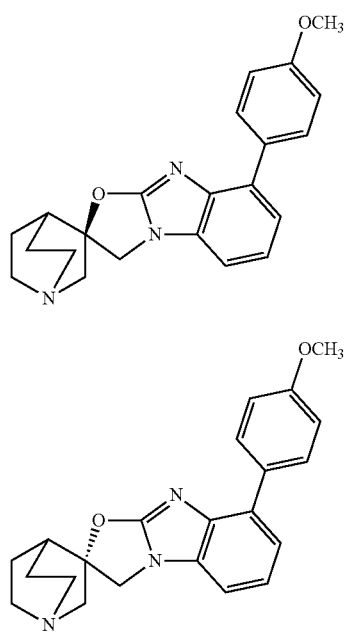

Step A: 3-Bromobenzene-1,2-diamine

To 3-bromo-2-nitroaniline (5 g, 23 mmol) in MeOH (45 mL) was added iron (3.9 g, 69 mmol) and acetic acid (1.2 mL, 21 mmol) at 0° C. The mixture was warmed to room temperature and stirred overnight. After completion of the reaction, the solids were filtered off, the filtrate was cooled with ice water, basified with ammonium hydroxide, extracted with ethyl acetate, washed with brine, dried over MgSO$_4$, filtered and the solvent removed under reduced pressure. The crude material was purified by chromatography (Biotage) to yield 3-bromobenzene-1,2-diamine (3.2 g, 16 mmol, 70% yield) as purple oil which slowly solidified upon standing. $^1$H NMR (500 MHz, DMSO-d$_6$) δ 6.72-6.62 (m, 1H), 6.51 (dd, J=7.8, 1.4 Hz, 1H), 6.41-6.26 (m, 1H), 4.94-4.71 (m, 2H), 4.66-4.46 (m, 2H). MS (LC/MS) R.T.=1.74; [M+1]$^+$=188.91.

Step B: 4-Bromo-1H-benzo[d]imidazol-2(3H)-one

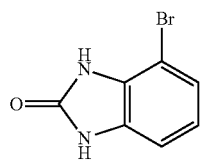 [SMILES: O=c1[nH]c2cccc(Br)c2[nH]1]

To a solution of 3-bromobenzene-1,2-diamine (3.1 g, 16 mmol) from example 12, step A, in anhydrous THF (30 mL) was added CDI (5.32 g, 33 mmol). The reaction mixture was stirred at room temperature overnight. The solvent was removed under reduced pressure and the residue was taken up in 2 N HCl. The precipitate was filtered and washed with water. The solids were dried in a vacuum oven (~90° C.) to yield a cream-colored powder, 4-bromo-1H-benzo[d]imidazol-2(3H)-one (2.7 g, 11 mmol, 70% yield). The product was carried on to the next step without any further purification. MS (LC/MS) R.T.=2.63; [M+1]$^+$=214.87.

Step C: 4-(4-Methoxyphenyl)-1H-benzo[d]imidazol-2(3H)-one

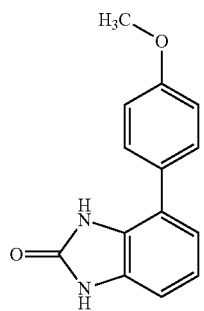 [SMILES: COc1ccc(-c2cccc3[nH]c(=O)[nH]c23)cc1]

To 4-bromo-1H-benzo[d]imidazol-2(3H)-one (1.47 g, 6.9 mmol) from example 12, step B, (4-methoxyphenyl)boronic acid (1.26 g, 8.3 mmol), and PdCl$_2$(dppf)-CH$_2$Cl$_2$ adduct (0.45 g, 0.55 mmol) in dioxane (60 mL) was added 2 N Na$_2$CO$_3$ (10.4 mL, 21 mmol). The reaction was heated to 90° C. for 4.0 hours and then cooled to RT. TLC showed a lower and a higher component. The reaction was diluted with water and extracted with ethyl acetate. The organics were dried with MgSO$_4$, filtered and the solvent was removed to yield the crude material. The material was semi-purified by chromatography (Biotage) to yield 4-(4-methoxyphenyl)-1H-benzo[d]imidazol-2(3H)-one (1.70 g, 7.1 mmol, 103% yield) as a powder. MS (LC/MS) R.T.=3.37; [M+]$^+$=240.99.

Step D: 2-Chloro-(4-methoxyphenyl)-1H-benzo[d]imidazole

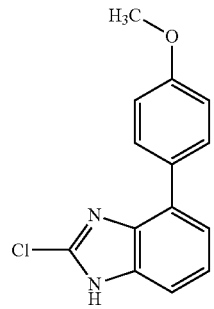 [SMILES: COc1ccc(-c2cccc3[nH]c(Cl)nc23)cc1]

To 4-(4-methoxyphenyl)-1H-benzo[d]imidazol-2(3H)-one (1.7 g, 7.1 mmol) from example 13, step C was added POCl$_3$ (13.9 ml, 150 mmol). The reaction mixture stirred and was heated to 120° C. for 2.5 hours. The reaction mixture was cooled to room temperature and stirred overnight. The excess POCl$_3$ was removed in vacuo and the left over residue was cooled in an ice bath. Ethyl acetate was added and dropwise addition of water. Once all the residue was in solution, it was then poured into a flask of ice water (~100 mL). The mixture was allowed to warm to room temperature and carefully neutralized with saturated NaHCO$_3$. The organics were separated, dried with MgSO$_4$, filtered, and the solvent was removed to yield the crude product. The crude product was purified by chromatography (Biotage) to yield 2-chloro-7-(4-methoxyphenyl)-1H-benzo[d]imidazole (1.5 g, 5.8 mmol, 82% yield) as a powder. $^1$H NMR (500 MHz, DMSO-d$_6$) δ 7.97 (d, J=8.5 Hz, 2H), 7.57 (d, J=7.8 Hz, 1H), 7.39 (d, J=7.8 Hz, 2H), 7.35-7.20 (m, 1H), 7.06 (d, J=8.7 Hz, 2H), 3.88-3.74 (m, 3H). MS (LC/MS) R.T.=3.64; [M+]$^+$=258.94.

Step E: (8-(4-Methoxyphenyl)-3H-1'-azaspiro[benzo[4,5]imidazo[2,1-b]oxazole-2,3'-bicyclo[2.2.2]octan]-1'-yl-8-ium)trihydroborate

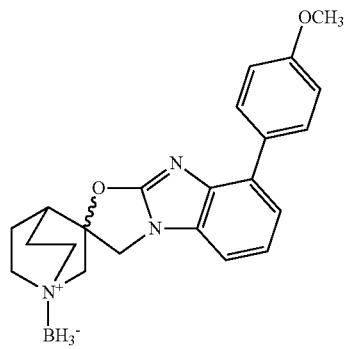

To 2-chloro-7-(4-methoxyphenyl)-1H-benzo[d]imidazole (0.42 g, 1.6 mmol) from example 12, step D, in THF (35 mL) was added n-butyllithium (0.65 mL, 1.6 mmol) dropwise at −78° C. After 45 minutes, a solution of racemic (1'-azaspiro[oxirane-2,3'-bicyclo[2.2.2]octan]-1'-yl-4-ium) trihydroborate (0.27 g, 1.8 mmol) from the reference example, in THF (10 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield racemic (8-(4-methoxyphenyl)-3H-1'-azaspiro[benzo[4,5]imidazo[2,1-b]oxazole-2,3'-bicyclo[2.2.2]octan]-1'-yl-10-ium)trihydroborate (0.29 g, 0.77 mmol, 47.6% yield). (Only one regioisomer was obtained.) The product was taken on to the next step without further purification.

Step F: (R)-8-(4-Methoxyphenyl)-3H-1'-azaspiro[benzo[4,5]imidazo[2,1-b]oxazole-2,3'-bicyclo[2.2.2]octane] and (S)-8-(4-methoxyphenyl)-3H-1'-azaspiro[benzo[4,5]imidazo[2,1-b]oxazole-2,3'-bicyclo[2.2.2]octane]

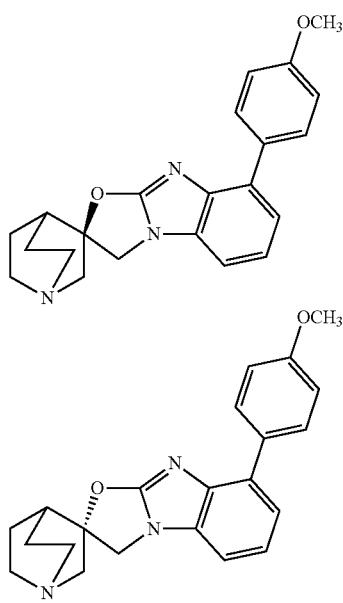

To racemic (8-(4-methoxyphenyl)-3H-1'-azaspiro[benzo[4,5]imidazo[2,1-b]oxazole-2,3'-bicyclo[2.2.2]octan]-1'-yl-10-ium)trihydroborate (0.3 g, 0.8 mmol) from example 12, step E, in acetone (10 mL) was added 3 M hydrogen chloride (2.0 mL, 4.0 mmol) at room temperature. After 35 minutes, 1 N NaOH was added until the pH was ~8-9. The product was extracted with ethyl acetate, dried with MgSO$_4$, filtered and the solvent was removed to yield the deprotected racemic mixture. The racemic material was separated using a chiral column (Chiralpak AS 21×250 mm 10 u, inj. vol. 2000 uL, Isocratic, start % B: 18, flow rate 15 mL/min, stop time 18 min., solvent A: 0.1% diethylamine/heptane, solvent B: ethanol, wavelength 220 nm) to yield two peaks. The first peak had a RT=9.16 min and the second peak RT=11.89 min.

The solvent was removed from both pure compounds to yield (S)-8-(4-methoxyphenyl)-3H-1'-azaspiro[benzo[4,5]imidazo[2,1-b]oxazole-2,3'-bicyclo[2.2.2]octane] (0.04 g, 0.11 mmol, 13% yield) as peak 1 and (R)-8-(4-methoxyphenyl)-3H-1'-azaspiro[benzo[4,5]imidazo[2,1-b]oxazole-2,3'-bicyclo[2.2.2]octane] (0.03 g, 0.079 mmol, 9.9% yield) as peak 2. Both were white powders. (S)-8-(4-methoxyphenyl)-3H-1'-azaspiro[benzo[4,5]imidazo[2,1-b]oxazole-2,3'-bicyclo[2.2.2]octane]. $^1$H NMR (500 MHz, DMSO-d$_6$) δ 8.02-7.87 (m, 1H), 7.29 (dd, J=7.6, 1.2 Hz, 1H), 7.23-7.19 (m, 1H), 7.17-7.11 (m, 1H), 7.05-6.94 (m, 2H), 4.54 (d, J=9.5 Hz, 1H), 4.26 (d, J=9.6 Hz, 1H), 3.22-3.09 (m, 2H), 2.89-2.79 (m, 2H), 2.77-2.66 (m, 2H), 2.29-2.18 (m, 1H), 2.05-1.87 (m, 1H), 1.68 (d, J=5.5 Hz, 2H), 1.59-1.48 (m, 1H). MS (LC/MS) R.T.=2.90; [M+]$^+$=362.28. Optical Rotation=+25.62°. (R)-8-(4-methoxyphenyl)-3H-1'-azaspiro[benzo[4,5]imidazo[2,1-b]oxazole-2,3'-bicyclo[2.2.2]octane]. $^1$H NMR (500 MHz, DMSO-d$_6$) δ 8.07-7.87 (m, 1H), 7.29 (dd, J=7.6, 1.2 Hz, 1H), 7.22-7.17 (m, 1H), 7.18-7.10 (m, 1H), 7.05-6.93 (m, 2H), 4.54 (d, J=9.5 Hz, 1H), 4.26 (d, J=9.6 Hz, 1H), 3.26-3.13 (m, 2H), 2.89-2.79 (m, 2H), 2.76-2.66 (m, 2H), 2.26 (d, J=2.7 Hz, 1H), 1.96 (d, J=4.9 Hz, 1H), 1.68 (br. s., 2H), 1.59-1.44 (m, 1H). MS (LC/MS) R.T.=2.92; [M+1]$^+$=362.28. Optical Rotation=−29.99°.

EXAMPLE 13

(R)-7-(Pyridin-3-yl)-3H-1'-azaspiro[benzo[4,5]imidazo[2,1-b]oxazole-2,3'-bicyclo[2.2.2]octane] and (S)-7-(Pyridin-3-yl)-3H-1'-azaspiro[benzo[4,5]imidazo[2,1-b]oxazole-2,3'-bicyclo[2.2.2]octane]

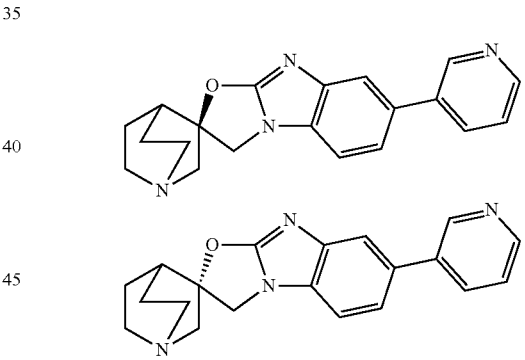

Step A: (7-Bromo-3H-1'-azaspiro[benzo[4,5]imidazo[2,1-b]oxazole-2,3'-bicyclo[2.2.2]octan]-1'-yl-10-ium)trihydroborate and (6-bromo-3H-1'-azaspiro[benzo[4,5]imidazo[2,1-b]oxazole-2,3'-bicyclo[2.2.2]octan]-1'-yl-10-ium)trihydroborate

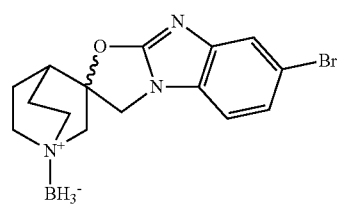

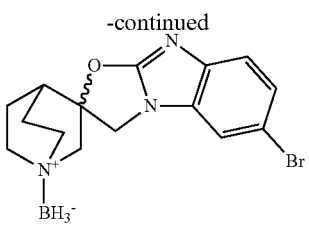

To 6-bromo-2-chloro-1H-benzo[d]imidazole (0.72 g, 3.1 mmol) in THF (15 mL) was added n-butyllithium (1.24 mL, 3.1 mmol) dropwise at −78° C. After 45 minutes, a solution of racemic (1-azaspiro[oxirane-2,3'-bicyclo[2.2.2]octan]-1'-yl-4-ium)trihydroborate (0.52 g, 3.4 mmol) from the reference example, in THF (15 mL) was added dropwise at −78° C. The cooling bath was removed and the reaction mixture warmed to room temperature. After 15 minutes, the mixture was heated to 75° C. for 2 hours and then cooled to room temperature. The reaction was quenched with water and the product was extracted with ethyl acetate (100 mL). The organics were dried with MgSO$_4$, filtered and the solvent was removed to yield the crude product. The crude material was purified by chromatography (Biotage) to yield a mixture of racemic regioisomers, (6-bromo-3H-1'-azaspiro[benzo[4,5]imidazo[2,1-b]oxazole-2,3'-bicyclo[2.2.2]octan]-1'-yl-10-ium)trihydroborate and (7-bromo-3H-1'-azaspiro[benzo[4,5]imidazo[2,1-b]oxazole-2,3'-bicyclo[2.2.2]octan]-1'-yl-10-ium)trihydroborate (0.51 g, 1.44 mmol, 46% yield) as one product.

Step B: (R)-7-(Pyridin-3-yl)-3H-1'-azaspiro[benzo[4,5]imidazo[2,1-b]oxazole-2,3'-bicyclo[2.2.2]octane] and (S)-7-(pyridin-3-yl)-3H-1'-azaspiro[benzo[4,5]imidazo[2,1-b]oxazole-2,3'-bicyclo[2.2.2]octane]

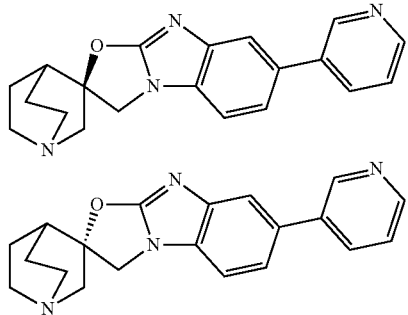

To the racemic regioisomers from Step A, Example 13 (0.51 g, 1.5 mmol), 3-(4,4,5,5-tetramethyl-1,3,2-dioxaborolan-2-yl)pyridine (0.36 g, 1.76 mmol), and PdCl$_2$(dppf)-CH$_2$Cl$_2$ adduct (0.096 g, 0.117 mmol) in dioxane (20 mL) was added 2 N Na$_2$CO$_3$ (7.33 mL, 14.65 mmol). The reaction was heated to 90° C. for 4.5 hours and then cooled to RT. The reaction was diluted with water and extracted with ethyl acetate. The organics were dried with MgSO$_4$, filtered and the solvent was removed to yield the crude material. The material was partially purified by chromatography (Biotage) to yield a residue, which was then subjected to chiral chromatography (Chiralcel OJ 21×250 mm 10 u, inj vol. 2000 uL, isocratic, start % B=20, flow rate 15 ml/min, stop time 37 min., solvent A: 0.1% diethylamine/heptane, solvent B: ethanol, wavelength 220 nm) to yield a peak that came off early (not product), then peak 1(RT=15.2 min), peak 2 and 3, which came off as a mixture (RT=19.6 and 21.2 min), and peak 4 (RT=26.9 min). The solvent was removed to yield peak 1 and peak 4. Peak 1 was determined to be (S)-7-(pyridin-3-yl)-3H-1'-azaspiro[benzo[4,5]imidazo[2,1-b]oxazole-2,3'-bicyclo [2.2.2]octane] (0.006 g, 0.018 mmol, 1.2% yield). $^1$H NMR (500 MHz, DMSO-d$_6$) δ 8.90 (d, J=2.3 Hz, 1H), 8.53 (dd, J=4.7, 1.4 Hz, 1H), 8.11-8.01 (m, 1H), 7.67 (s, 1H), 7.57-7.35 (m, 3H), 4.56 (d, J=9.8 Hz, 1H), 4.27 (d, J=9.8 Hz, 1H), 3.22 (s, 2H), 2.84 (s, 2H), 2.73 (s, 2H), 2.31-2.21 (m, 1H), 2.06-1.88 (m, 1H), 1.76-1.61 (m, 2H), 1.61-1.46 (m, 1H). MS (LC/MS) R.T.=1.30; [M+1]$^+$=333.23. Peak 4 was determined to be (R)-7-(pyridin-3-yl)-3H-1'-azaspiro[benzo[4,5]imidazo[2,1-b]oxazole-2,3'-bicyclo[2.2.2]octane] (0.007 g, 0.020 mmol, 1.4% yield). $^1$H NMR (500 MHz, DMSO-d$_6$) δ 8.89 (d, J=2.0 Hz, 1H), 8.52 (dd, J=4.7, 1.4 Hz, 1H), 8.07 (dt, J=7.9, 1.9 Hz, 1H), 7.73 (d, J=1.4 Hz, 1H), 7.53-7.34 (m, 3H), 4.57 (d, J=9.6 Hz, 1H), 4.28 (d, J=9.8 Hz, 1H), 3.29-3.21 (m, 2H), 2.87 (t, J=7.7 Hz, 1H), 2.76 (t, J=7.8 Hz, 1H), 2.29 (br. s., 1H), 2.05-1.91 (m, 1H), 1.70 (br. s., 2H), 1.62-1.47 (m, 1H). MS (LC/MS) R.T.=1.31; [M+1]$^+$=333.13. Both were yellow powders.

EXAMPLE 14

(R)-2-Phenyl-6H-1'-azaspiro[oxazolo[3,2-b][1,2,4]triazole-5,3'-bicyclo [2.2.2]octane] and (S)-2-Phenyl-6H-1'-azaspiro[oxazolo[3,2-b][1,2,4]triazole-5,3'-bicyclo [2.2.2]octane]

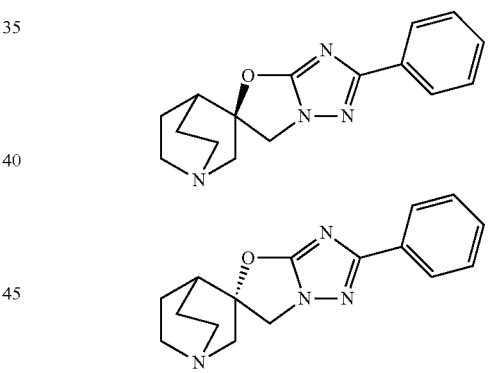

NaH (13.1 mg, 0.33 mmol) was added to a stirred solution of 3-bromo-5-phenyl-4H-1,2,4-triazole (73.2 mg, 0.33 mmol) in THF (1.6 mL) at ambient temperature under N$_2$ (g). After 15 min, racemic (1'-azaspiro[oxirane-2,3'-bicyclo [2.2.2]octan]-1'-yl-4-ium)trihydroborate (100 mg, 0.65 mmol) from the reference example, was added, and the reaction vessel was subsequently placed into a preheated oil bath. The reaction was stirred at 70° C. for 16 h before it was quenched with water (30 mL). The aqueous layer was extracted using chloroform (3×75 mL), and the combined organic layers were dried over sodium sulfate before the solids were filtered away. The volatiles were removed under reduced pressure, the crude material was loaded onto a Biotage silica-gel column, and the desired racemic product, (2-phenyl-6H-1'-azaspiro[oxazolo[3,2-b][1,2,4]triazole-5,3'-bicyclo[2.2.2]octan]-1'-yl-8-ium)trihydroborate (55.7 mg, 0.19 mmol, 58% yield) was isolated using ethyl acetate in hexanes (0-50%).

HCl (4 M in dioxane, 464 μL, 1.86 mmol) was added to a stirred solution of racemic (2-phenyl-6H-1'-azaspiro[oxazolo[3,2-b][1,2,4]triazole-5,3'-bicyclo[2.2.2]octan]-1'-yl-8-ium)trihydroborate (55.0 mg, 0.19 mmol) in 1.9 mL acetone, at ambient temperature, and the reaction was stirred for 30 min. The reaction was then neutralized with 1N NaOH to pH 8-9, and the product was extracted from the aqueous layer with chloroform (3×75 mL). The combined organic layers were dried over sodium sulfate, and the volatiles were removed under reduced pressure. The crude material was loaded onto a Biotage silica-gel column, and purified using ammonium hydroxide in methanol (10%) and chloroform (0-10%) to afford racemic 2-phenyl-6H-1'-azaspiro[oxazolo[3,2-b][1,2,4]triazole-5,3'-bicyclo[2.2.2]octane] (33.2 mg, 0.12 mmol, 63%) as a white solid. The enantiomers were separated using a Chiralpak OD-H (4.6×250 mm, 5 μm) column with a mobile phase consisting of 35% methanol (0.1% DEA) in $CO_2$. The wavelength was set at 215 nM. The separated peaks were concentrated in vacuo to yield the two enantiomers as white solids. $^1$H NMR (500 MHz, DMSO-$d_6$) 7.92-7.88 (m, 2H), 7.47-7.37 (m, 3H), 4.57 (d, J=9.8 Hz, 1H), 4.33 (d, J=9.8 Hz, 1H), 3.26-3.16 (m, 2H), 2.86-2.74 (m, 2H), 2.72-2.67 (m, 2H), 2.32-2.28 (m, 1H), 1.98-1.87 (m, 1H), 1.68-1.61 (m, 2H), 1.56-1.48 (m, 1H). MS (LC/MS) R.T.=1.23, [M+H]$^+$=283.1.

EXAMPLE 15

2-Bromo-6H-1'-azaspiro[oxazolo[3,2-b][1,2,4]triazole-5,3'-bicyclo[2.2.2]octane]

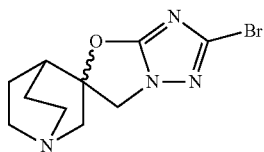 [SMILES: Brc1nc2n(n1)CC1(CN3CCC1CC3)O2]

NaH (26.1 mg, 0.65 mmol) was added to a stirred solution of 3,5-dibromo-4H-1,2,4-triazole (148 mg, 0.65 mmol) in THF (3.3 mL) at ambient temperature under $N_2$ (g). After 15 min, racemic (1'-azaspiro[oxirane-2,3'-bicyclo[2.2.2]octan]-1'-yl-4-ium)trihydroborate (200 mg, 1.31 mmol) from the reference example, was added, and the reaction vessel was subsequently placed into a preheated oil bath. The reaction was stirred at 70° C. for 16 h before it was quenched with water (30 mL). The aqueous layer was extracted using chloroform (3×75 mL), and the combined organic layers were dried over sodium sulfate before the solids were filtered away. The volatiles were removed under reduced pressure, the crude material was loaded onto a Biotage silica-gel column, and the desired racemic product, (2-bromo-6H-1'-azaspiro[oxazolo[3,2-b][1,2,4]triazole-5,3'-bicyclo[2.2.2]octan]-1'-yl-8-ium)trihydroborate (121 mg, 0.40 mmol, 62% yield) was isolated using ethyl acetate in hexanes (0-50%).

HCl (4 M in dioxane, 1.01 mL, 4.03 mmol) was added to a stirred solution of racemic (2-bromo-6H-1'-azaspiro[oxazolo[3,2-b][1,2,4]triazole-5,3'-bicyclo[2.2.2]octan]-1'-yl-8-ium)trihydroborate (121 mg, 0.4 mmol) in 4 mL acetone, at ambient temperature, and reaction was stirred for 30 min. At that time, the reaction was neutralized with 1N NaOH to pH 8-9, and the product was extracted from the aqueous layer with chloroform (3×75 mL). The combined organic layers were dried over sodium sulfate, and the volatiles were removed under reduced pressure. The crude material was loaded onto a Biotage silica-gel column, and purified using ammonium hydroxide in methanol (10%) and chloroform (0-10%) to afford racemic 2-bromo-6H-1'-azaspiro[oxazolo[3,2-b][1,2,4]triazole-5,3'-bicyclo[2.2.2]octane] (101 mg, 0.35 mmol, 86%) as a white solid. $^1$H NMR (400 MHz, methanol-$d_4$) δ 4.56 (d, J=9.5 Hz, 1H), 4.25 (d, J=9.8 Hz, 1H), 3.43-3.35 (m, 1H), 3.27-3.19 (m, 1H), 3.02-2.76 (m, 4H), 2.38-2.27 (m, 1H), 2.15-2.03 (m, 1H), 1.88-1.60 (m, 3H). MS (LC/MS) R.T.=0.47, [M+H]$^+$=286.9.

EXAMPLE 16

2-Chloro-6H-1'-azaspiro[oxazolo[3,2-b][1,2,4]triazole-5,3'-bicyclo[2.2.2]octane]

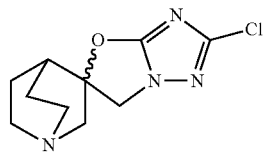

NaH (43.5 mg, 1.09 mmol) was added to a stirred solution of 3,5-dichloro-4H-1,2,4-triazole (150 mg, 1.1 mmol) in DMF (5.4 mL) at ambient temperature under $N_2$ (g). After 15 min, racemic (1'-azaspiro[oxirane-2,3'-bicyclo[2.2.2]octan]-1'-yl-4-ium)trihydroborate (200 mg, 1.31 mmol) from the reference example, was added, and the reaction vessel was subsequently placed into a preheated oil bath. The reaction was stirred at 100° C. for 16 h before it was quenched with water (30 mL). The aqueous layer was extracted using chloroform (3×75 mL), and the combined organic layers were dried over sodium sulfate before the solids were filtered away. The volatiles were removed under reduced pressure, the crude material was loaded onto a Biotage silica-gel column, and the desired racemic product, (2-chloro-6H-1'-azaspiro[oxazolo[3,2-b][1,2,4]triazole-5,3'-bicyclo[2.2.2]octan]-1'-yl-8-ium)trihydroborate (98.2 mg, 0.39 mmol, 36% yield) was isolated using ethyl acetate in hexanes (0-50%).

HCl (4 M in dioxane, 965 μL, 3.86 mmol) was added to a stirred solution of racemic (2-chloro-6H-1'-azaspiro[oxazolo[3,2-b][1,2,4]triazole-5,3'-bicyclo[2.2.2]octan]-1'-yl-8-ium)trihydroborate (98.2 mg, 0.39 mmol) in 3.9 mL acetone, at ambient temperature and the reaction was stirred for 30 min. Then the reaction was neutralized with 1N NaOH to pH 8-9, and the product was extracted from the aqueous layer with chloroform (3×75 mL). The combined organic layers were dried over sodium sulfate, and the volatiles were removed under reduced pressure. The crude material was loaded onto a Biotage silica-gel column, and purified using ammonium hydroxide in methanol (10%) and chloroform (0-10%) to afford racemic 2-chloro-6H-1'-azaspiro[oxazolo[3,2-b][1,2,4]triazole-5,3'-bicyclo[2.2.2]octane] (71.3 mg, 0.29 mmol, 75%) as a white solid. $^1$H NMR (400 MHz, methanol-$d_4$) δ 4.55 (d, J=9.8 Hz, 1H), 4.24 (d, J=9.8 Hz, 1H), 3.42-3.35 (m, 1H), 3.28-3.19 (m, 1H), 3.02-2.75 (m, 4H), 2.38-2.28 (m, 1H), 2.18-2.03 (m, 1H), 1.91-1.58 (m, 3H). MS (LC/MS) R.T.=0.42, [M+H]$^+$=241.0.

EXAMPLE 17

6H-1'-Azaspiro[oxazolo[3,2-b][1,2,4]triazole-5,3'-bicyclo[2.2.2]octane]

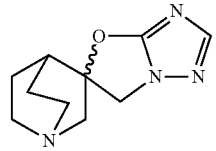 [SMILES: c1nc2n(n1)CC1(CN3CCC1CC3)O2]

Racemic 2-bromo-6H-1'-azaspiro[oxazolo[3,2-b][1,2,4]triazole-5,3'-bicyclo[2.2.2]octane] (20 mg, 0.07 mmol), from Example 15, 0.4 mL ethanol, and Pd/C (7.5 mg, 7 µmol) were stirred under a $H_2$ (g) atmosphere (balloon pressure) for 4 h at ambient temperature. The solids were filtered away with Celite, and the volatiles were removed from the filtrate under reduced pressure. The crude material was loaded onto a Biotage silica-gel column, and purified using ammonium hydroxide in methanol (10%) and chloroform (0-15%) to afford racemic 6H-1'-azaspiro[oxazolo[3,2-b][1,2,4]triazole-5,3'-bicyclo[2.2.2]octane] (5.0 mg, 0.02 mmol, 33% yield) as a white solid. $^1$H NMR (400 MHz, methanol-$d_4$) 7.65 (s, 1H), 4.55 (d, J=9.8 Hz, 1H), 4.25 (d, J=9.8 Hz, 1H), 3.44-3.36 (m, 1H), 3.29-3.20 (m, 1H), 3.03-2.77 (m, 4H), 2.39-2.29 (m, 1H), 2.20-2.04 (m, 1H), 1.90-1.60 (m, 3H). MS (LC/MS) R.T.=0.24, [M+H]$^+$=207.1.

EXAMPLE 18

7-Bromo-6-methyl-3H-1'-azaspiro[oxazolo[2',3':2,3]imidazo[4,5-b]pyridine-2,3'-bicyclo[2.2.2]octane]

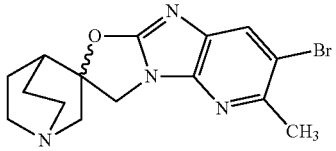 [SMILES: Cc1nc2c(cc1Br)nc1n2CC2(CN3CCC2CC3)O1]

Step A: 2,6-Dibromo-5-methyl-3H-imidazo[4,5-b]pyridine

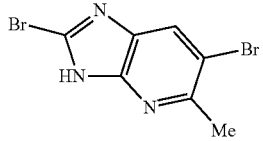 [SMILES: Cc1nc2[nH]c(Br)nc2cc1Br]

5-Methyl-1H-imidazo[4,5-b]pyridine-2(3H)-thione (34.4 mg, 0.208 mmol) was added to a stirred solution of aqueous HBr (48%, 30.6 µl, 0.271 mmol) and acetic acid (833 µl) at ambient temperature. Bromine (39 µl, 0.75 mmol) was added dropwise and the reaction was stirred for 3 h. The reaction mixture was neutralized with aqueous NaOH (1N), and the product was extracted into chloroform (3×50 mL). The volatiles were removed under reduced pressure, and the crude material was purified by silica-gel column chromatography with ethyl acetate in hexanes (0-80%) to afford 2,6-dibromo-5-methyl-3H-imidazo[4,5-b]pyridine (13 mg, 0.04 mmol, 21% yield).

Step B: 7-Bromo-6-methyl-3H-1'-azaspiro[oxazolo[2',3':2,3]imidazo-[4,5-b]pyridine-2,3'-bicyclo[2.2.2]octane]

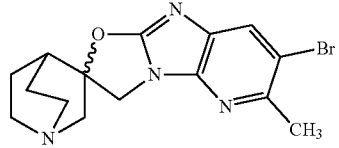 [SMILES: Cc1nc2c(cc1Br)nc1n2CC2(CN3CCC2CC3)O1]

NaH (1.8 mg, 0.089 mmol) was added to a stirred solution of 2,6-dibromo-5-methyl-3H-imidazo[4,5-b]pyridine (13 mg, 0.045 mmol) in THF (220 µL) at ambient temperature under $N_2$ (g). After 15 min, racemic 1'-azaspiro[oxirane-2,3'-bicyclo[2.2.2]octan]-1'-yl-4-iumtrihydroborate (13.7 mg, 0.09 mmol) from the reference example, was added, and the reaction vessel was subsequently placed into a preheated oil bath. The reaction was stirred at 70° C. for 16 h before it was quenched with water (40 mL). The aqueous layer was extracted using chloroform (3×50 mL), and the combined organic layers were dried over sodium sulfate before the solids were filtered away. The volatiles were removed under reduced pressure, the crude material was loaded onto a Biotage silica-gel column, and the desired racemic product, (7-bromo-6-methyl-3H-1'-azaspiro[oxazolo[2',3':2,3]imidazo[4,5-b]pyridine-2,3'-bicyclo[2.2.2]octan]-1'-yl-10-ium)trihydroborate (5.1 mg, 0.01 mmol, 31% yield) was isolated using ethyl acetate in hexanes (0-80%).

HCl (4 M in dioxane, 35 µL, 0.14 mmol) was added to a stirred solution of racemic (7-bromo-6-methyl-3H-1'-azaspiro[oxazolo[2',3':2,3]imidazo[4,5-b]pyridine-2,3'-bicyclo[2.2.2]octan]-1'-yl-10-ium)trihydroborate (5.1 mg, 0.014 mmol) in 0.14 mL acetone, at ambient temperature. The reaction was stirred for 30 min., then neutralized with 1N NaOH to pH 8-9, and the product was extracted from the aqueous layer with chloroform (3×75 mL). The combined organic layers were dried over sodium sulfate, and the volatiles were removed under reduced pressure. The crude material was loaded onto a Biotage silica-gel column, and purified using ammonium hydroxide in methanol (10%) and chloroform (0-10%) to afford racemic 7-bromo-6-methyl-3H-1'-azaspiro[oxazolo[2',3':2,3]imidazo-[4,5-b]pyridine-2,3'bicyclo-[2.2.2]octane] (4.6 mg, 0.01 mmol, 92%) as a white solid. $^1$H NMR (500 MHz, methanol-$d_4$) δ 7.89 (s, 1H), 4.62 (d, J=10.1 Hz, 1H), 4.28 (d, J=10.1 Hz, 1H), 3.50-3.43 (m, 1H), 3.32-3.27 (m, 1H), 3.39-3.27 (m, 2H), 3.04-2.96 (m, 2H), 2.94-2.84 (m, 2H), 2.67 (s, 3H), 2.39-2.35 (m, 1H), 2.21-2.13 (m, 1H), 1.93-1.78 (m, 2H), 1.76-1.67 (m, 1H). MS (LC/MS) R.T.=1.40, [M+H]$^+$=351.0.

EXAMPLE 19

7-Bromo-3H-1'-azaspiro[oxazolo[2',3':2,3]imidazo[4,5-b]pyridine-2,3'-bicyclo[2.2.2]octane]

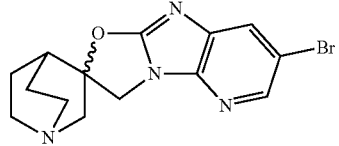 [SMILES: Brc1cnc2c(c1)nc1n2CC2(CN3CCC2CC3)O1]

NaH (1.4 mg, 0.03 mmol) was added to a stirred solution of 6-bromo-2-chloro-3H-imidazo[4,5-b]pyridine (7.4 mg, 0.03 mmol) in DMF (159 mL) at ambient temperature under N₂ (g). After 15 min, racemic (1'-azaspiro[oxirane-2,3'-bicyclo[2.2.2]octan]-1'-yl-4-ium)trihydroborate (5.9 mg, 0.048 mmol) from example 1, was added, and the reaction vessel was subsequently placed into a preheated oil bath. The reaction was stirred at 70° C. for 16 h before it was quenched with water (40 mL). The aqueous layer was extracted using chloroform (3×50 mL), the combined organic layers were dried over sodium sulfate before the solids were filtered away, and the volatiles were removed under reduced pressure. The crude reaction mixture was diluted with acetone (5 mL), and HCl (4N in dioxane, 2 mL) was added at ambient temperature. The reaction mixture was stirred at that temperature for 30 min before it was neutralized with 1N NaOH to pH 8-9, and the product was extracted from the aqueous layer with chloroform (3×40 mL). The combined organic layers were dried over sodium sulfate, and the volatiles were removed under reduced pressure. The crude material was loaded onto a Biotage silica-gel column, and purified using ammonium hydroxide in methanol (10%) and chloroform (0-15%) to afford racemic 7-bromo-3H-1'-azaspiro[oxazolo[2',3':2,3]imidazo[4,5-b]pyridine-2,3'-bicyclo[2.2.2]octane] (1.8 mg, 0.0051 mmol, 16%) as a white solid. ¹H NMR (400 MHz, methanol-d₄) δ 8.19 (d, J=2.0 Hz, 1H), 7.89 (d, J=2.0 Hz, 1H), 4.63 (d, J=10.0 Hz, 1H), 4.29 (d, J=10.0 Hz, 1H), 3.49-3.41 (m, 1H), 3.30-3.26 (m, 1H), 3.04-2.94 (m, 2H), 2.91-2.83 (m, 2H), 2.42-2.33 (m, 1H), 2.26-2.06 (m, 1H), 1.93-1.65 (m, 3H). MS (LC/MS) R.T.=1.22, [M+H]⁺=336.9.

EXAMPLE 20

7-Chloro-3H-1'-azaspiro[oxazolo[2',3':2,3]imidazo[4,5-b]pyridine-2,3'-bicyclo[2.2.2]octane]

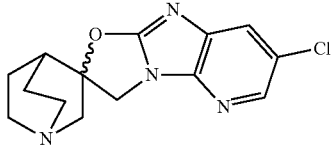 [SMILES: Clc1cnc2c(c1)nc1n2CC2(CN3CCC2CC3)O1]

NaH (9.5 mg, 0.24 mmol) was added to a stirred solution of 2,6-dichloro-3H-imidazo[4,5-b]pyridine (45 mg, 0.24 mmol) in THF (3.0 mL) at ambient temperature under N₂ (g). After 15 min, racemic (1'-azaspiro[oxirane-2,3'-bicyclo[2.2.2]octan]-1'-yl-4-ium)trihydroborate (72 mg, 0.47 mmol), from the reference example, was added, and the reaction vessel was subsequently placed into a preheated oil bath. The reaction was stirred at 70° C. for 72 h before it was quenched with water (20 mL). The aqueous layer was extracted using chloroform (3×30 mL), and the combined organic layers were dried over sodium sulfate before the solids were filtered off. The volatiles were removed under reduced pressure, the crude material was loaded onto a Biotage silica-gel column, and the desired racemic product, (7-chloro-3H-1'-azaspiro[oxazolo[2',3':2,3]imidazo[4,5-b]pyridine-2,3'-bicyclo[2.2.2]octan]-1'-yl-10-ium)trihydroborate (28 mg, 0.09 mmol, 39% yield) was isolated using ethyl acetate in hexanes (30-70%).

HCl (4 M in dioxane, 230 µL, 0.92 mmol) was added to a stirred solution of racemic (7-chloro-3H-1'-azaspiro[oxazolo[2',3':2,3]imidazo[4,5-b]pyridine-2,3'-bicyclo[2.2.2]octan]-1'-yl-10-ium)trihydroborate (28 mg, 0.09 mmol) in 0.9 mL acetone, at ambient temperature. The reaction was stirred at that temperature for 1 h. At that time, the reaction was neutralized with 1N NaOH to pH 8-9, and the product was extracted from the aqueous layer with chloroform (3×25 mL). The combined organic layers were dried over sodium sulfate, and the volatiles were removed under reduced pressure. The crude material was purified using reverse-phase preparatory HPLC (acetonitrile/water/ammonium acetate) to afford racemic 7-chloro-3H-1'-azaspiro[oxazolo[2',3':2,3]imidazo[4,5-b]pyridine-2,3'-bicyclo[2.2.2]octane] (4.6 mg, 0.015 mmol, 17%) as an off-white solid. ¹H NMR (400 MHz, acetone) δ 8.04 (d, J=2.0 Hz, 1H), 7.70 (d, J=2.0 Hz, 1H), 4.65 (d, J=10.0 Hz, 1H), 4.34 (d, J=10.0 Hz, 1H), 3.43-3.29 (m, 2H), 2.93 (t, J=7.8 Hz, 2H), 2.84 (t, J=7.8 Hz, 2H), 2.43-2.37 (m, 1H), 2.14-2.08 (m, 1H), 1.92-1.74 (m, 2H), 1.68-1.57 (m, 1H). MS (LC/MS) R.T.=1.50, [M+H]⁺=291.2.

EXAMPLE 21

(R)-6-Phenyl-3H-1'-azaspiro[imidazo[2,1-b]oxazole-2,3'-bicyclo[2.2.2]octane] and (S)-6-phenyl-3H-1'-azaspiro[imidazo[2,1-b]oxazole-2,3'-bicyclo[2.2.2]octane]

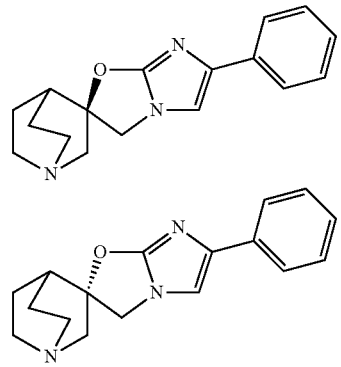

To a stirring solution of 197.3 mg 2-chloro-4-phenyl-1H-imidazole (1.1 mmol) in 5 mL tetrahydrofuran was added 173 mg 60% sodium hydride (4.3 mmol) and the mixture was stirred at room temperature for ~10 minutes. Then was added 242 mg (1'-azaspiro[oxirane-2,3'-bicyclo[2.2.2]octan]-1'-yl-4-iumtrihydroborate (1.6 mmol) and the resulting mixture was stirred at room temperature for 15 minutes, then heated overnight in an oil bath at 75° C. The reaction was then removed from the heat, evaporated in vacuo, and the residue was subjected to a silica gel column in 50% ethyl acetate/hexane, collecting the main component. The two enantiomers (M1, M2) were separated on a Chiralpak AD column (Conditions: Chiralpak AD column 21×250 mm; 10 uM; 55% ethanol:45% (0.1% diethylamine/heptane); 15 mL/min flow rate; peaks center at 10.4 and 13.3 min). The two enantiomers were separately dissolved in 10 mL acetone and treated with 1.5 mL 3M HCl solution. Each mixture was then neutralized by the addition of aqueous sodium hydroxide, extracted into ethyl acetate, the ethyl acetate fractions dried over magnesium sulfate, filtered, and evaporated to the impure enantiomers M1 and M2. Each was subjected to preparative HPLC, collecting the main components, which were neutralized by passing them down a silica column in 1% ammonium hydroxide/9% MeOH/90% CHCl3 to give the final products M1 ((R)-6-phenyl-3H-1'-azaspiro[imidazo[2,1-b]oxazole-2,3'-bicyclo[2.2.2]octane]) (15 mg) (clear oil). MS (LC/MS; column: X-Bridge C-18 2.1×50 mm; 3.5 uM) R.T.=1.48; [M+1]⁺=282.29; Chiral HPLC (column: Chiralcel OD-H, 4.6×100 mm, 5 uM; 20% ethanol/80% (0.1% diethylamine/heptane)); RT 7.51 min;

$^1$H NMR (500 MHz, methanol-$d_4$) δ ppm 1.64-1.91 (m, 3H) 2.12-2.24 (m, 1H) 2.27-2.33 (m, 1H) 2.84-2.94 (m, 2H) 2.97-3.04 (m, 2H) 3.26 (d, J=15.11 Hz, 1H) 3.33 (dt, J=3.24, 1.66 Hz, 4H) 3.40 (dd, J=15.11, 1.53 Hz, 1H) 4.11 (d, J=10.22 Hz, 1H) 4.44 (d, J=10.22 Hz, 1H) 7.11 (s, 1H) 7.17-7.25 (m, 1H) 7.29-7.36 (m, 1H) 7.58-7.66 (m, 1H) and M2 ((S)-6-phenyl-3H-1'-azaspiro[imidazo[2,1-b]oxazole-2,3'-bicyclo[2.2.2]octane]) (21 mg). (clear oil) MS (LC/MS; column: X-Bridge C-18 2.1×50 mm; 3.5 uM) R.T.=1.58; [M+1]⁺=282.30; Chiral HPLC (column: Chiralcel OD-H, 4.6×100 mm, 5 uM; 20% ethanol/80% (0.1% diethylamine/ heptane)); RT 5.09 min; $^1$H NMR (500 MHz, methanol-$d_4$) δ ppm 1.94-2.07 (m, 2H) 2.08-2.18 (m, 1H) 2.34-2.45 (m, 1H) 2.59 (dt, J=4.01, 2.04 Hz, 1H) 3.25-3.38 (m, 6H) 3.74 (dd, J=14.80, 2.29 Hz, 1H) 3.89 (dd, J=14.65, 1.68 Hz, 1H) 4.26 (d, J=10.38 Hz, 1H) 4.53 (d, J=10.38 Hz, 1H) 7.17 (s, 1H) 7.22 (tt, J=7.40, 1.22 Hz, 1H) 7.31-7.38 (m, 1H) 7.58-7.68 (m, 1H)

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula I

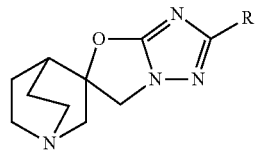

wherein
X is N— or C—$R_1$;
R is H, $C_1$-$C_6$ alkyl, halo, halo $C_1$-$C_6$ alkyl, phenyl, substituted phenyl;
$R_1$ is H, $C_1$-$C_6$ alkyl, halo, halo $C_1$-$C_6$ alkyl, phenyl, substituted phenyl, or
R and $R_1$ can be taken together to form an aryl or heteroaryl ring, which may be further substituted by 1-3 substituents independently selected from $C_1$-$C_6$ alkyl, halo, halo $C_1$-$C_6$ alkyl, alkoxy, trifluoromethyl, phenyl, substituted phenyl or pyridyl;
or a pharmaceutically acceptable salt or stereoisomer thereof.

2. The compound according to claim 1 of formula II

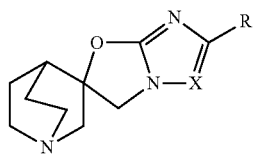

wherein
R and $R_1$ are independently H, $C_1$-$C_6$ alkyl, halo, halo $C_1$-$C_6$ alkyl, phenyl, substituted phenyl, or
R and $R_1$ can be taken together to form an aryl or heteroaryl ring, which may be further substituted by 1-3 substituents independently selected from $C_1$-$C_6$ alkyl, halo, halo $C_1$-$C_6$ alkyl, alkoxy, trifluoromethyl, phenyl, substituted phenyl or pyridyl;
or a pharmaceutically acceptable salt or stereoisomer thereof.

3. The compound according to claim 1 of formula III

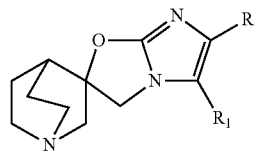

wherein
R is H, $C_1$-$C_6$ alkyl, halo, halo $C_1$-$C_6$ alkyl, phenyl, or substituted phenyl;
or a pharmaceutically acceptable salt or stereoisomer thereof.

4. The compound according to claim 2 wherein R and $R_1$ are independently H, halo, $C_1$-$C_3$ alkyl or phenyl; or a pharmaceutically acceptable salt or stereoisomer thereof.

5. The compound according to claim 2 wherein R and $R_1$ are taken together to form an aryl or heteroaryl ring, which may be further substituted by 1-3 substituents independently selected from $C_1$-$C_6$ alkyl, halo, halo $C_1$-$C_6$ alkyl, alkoxy, $CF_3$, phenyl, substituted phenyl or pyridyl; or a pharmaceutically acceptable salt or stereoisomer thereof.

6. The compound according to claim 1 wherein R and $R_1$ are taken together to form a phenyl ring which may be further substituted by 1-3 substituents independently selected from $C_1$-$C_6$ alkyl, halo, halo $C_1$-$C_6$ alkyl, $C_1$-$C_6$ alkoxy, $CF_3$, phenyl, substituted phenyl or pyridyl; or a pharmaceutically acceptable salt or stereoisomer thereof.

7. The compound according to claim 1 wherein R and $R_1$ are taken together to form a phenyl ring which may be further substituted by 1-3 substituents independently selected from $CH_3$, Cl, Br, $OCH_3$, $CF_3$, phenyl, phenyl substituted with $CH_3$ or phenyl substituted with pyridyl; or a pharmaceutically acceptable salt or stereoisomer thereof.

8. The compound according to claim 6 wherein R and $R_1$ are taken together to form a pyridyl ring which may be further substituted by 1-2 substituents independently selected from $C_1$-$C_3$ alkyl or halo; or a pharmaceutically acceptable salt or stereoisomer thereof.

9. The compound according to claim 1 wherein R and $R_1$ are taken together to form a pyridyl ring which may be further substituted by 1-2 substituents independently selected from Br, Cl or $CH_3$.

10. The compound according to claim 3 wherein R is H, halo or phenyl; or a pharmaceutically acceptable salt or stereoisomer thereof.

11. A compound according to claim 1 selected from the following
(R)-5,6-dibromo-3H-1'-azaspiro[imidazo[2,1-b]oxazole-2,3'-bicyclo[2.2.2]octane];
(S)-5,6-dibromo-3H-1'-azaspiro[imidazo[2,1-b]oxazole-2,3'-bicyclo[2.2.2]octane];
(R)-5,6-dichloro-3H-1'-azaspiro[imidazo[2,1-b]oxazole-2,3'-bicyclo[2.2.2]octane];
(S)-5,6-dichloro-3H-1'-azaspiro[imidazo[2,1-b]oxazole-2,3'-bicyclo[2.2.2]octane];
5-bromo-6-methyl-3H-1'-azaspiro[imidazo[2,1-b]oxazole-2,3'-bicyclo[2.2.2]octane];

6-bromo-5-methyl-3H-1'-azaspiro[imidazo[2,1-b]oxazole-2,3'-bicyclo[2.2.2]octane];
(R)-3H-1'-azaspiro[benzo[4,5]imidazo[2,1-b]oxazole-2,3'-bicyclo[2.2.2]octane];
(S)-3H-1'-azaspiro[benzo[4,5]imidazo[2,1-b]oxazole-2,3'-bicyclo[2.2.2]octane];
(R)-6,7-dimethyl-3H-1'-azaspiro[benzo[4,5]imidazo[2,1-b]oxazole-2,3'-bicyclo[2.2.2]octane];
(S)-6,7-dimethyl-3H-1'-azaspiro[benzo[4,5]imidazo[2,1-b]oxazole-2,3'-bicyclo[2.2.2]octane];
(R)-7-methoxy-3H-1'-azaspiro[benzo[4,5]imidazo[2,1-b]oxazole-2,3'-bicyclo[2.2.2]octane];
(S)-7-methoxy-3H-1'-azaspiro[benzo[4,5]imidazo[2,1-b]oxazole-2,3'-bicyclo[2.2.2]octane];
(R)-6-methoxy-3H-1'-azaspiro[benzo[4,5]imidazo[2,1-b]oxazole-2,3'-bicyclo[2.2.2]octane];
(S)-6-methoxy-3H-1'-azaspiro[benzo[4,5]imidazo[2,1-b]oxazole-2,3'-bicyclo[2.2.2]octane];
(R)-7-methyl-3H-1'-azaspiro[benzo[4,5]imidazo[2,1-b]oxazole-2,3'-bicyclo[2.2.2]octane];
(S)-7-methyl-3H-1'-azaspiro[benzo[4,5]imidazo[2,1-b]oxazole-2,3'-bicyclo[2.2.2]octane];
(R)-6-methyl-3H-1'-azaspiro[benzo[4,5]imidazo[2,1-b]oxazole-2,3'-bicyclo[2.2.2]octane];
(S)-6-methyl-3H-1'-azaspiro[benzo[4,5]imidazo[2,1-b]oxazole-2,3'-bicyclo[2.2.2]octane];
(R)-7-(trifluoromethyl)-3H-1'-azaspiro[benzo[4,5]imidazo[2,1-b]oxazole-2,3'-bicyclo[2.2.2]octane];
(S)-7-(trifluoromethyl)-3H-1'-azaspiro[benzo[4,5]imidazo[2,1-b]oxazole-2,3'-bicyclo[2.2.2]octane];
(R)-6-(trifluromethyl)-3H-1'-azaspiro[benzo[4,5]imidazo[2,1-b]oxazole-2,3'-bicyclo[2.2.2]octane];
(S)-6-(trifluoromethyl)-3H-1'-azaspiro[benzo[4,5]imidazo[2,1-b]oxazole-2,3'-bicyclo[2.2.2]octane];
(R)-8-chloro-3H-1'-azaspiro[benzo[4,5]imidazo[2,1-b]oxazole-2,3'-bicyclo[2.2.2]octane];
(S)-8-chloro-3H-1'-azaspiro[benzo[4,5]imidazo[2,1-b]oxazole-2,3'-bicyclo[2.2.2]octane];
(R)-5-chloro-3H-1'-azaspiro[benzo[4,5]imidazo[2,1-b]oxazole-2,3'-bicyclo[2.2.2]octane],
(S)-5-chloro-3H-1'-azaspiro[benzo[4,5]imidazo[2,1-b]oxazole-2,3'-bicyclo[2.2.2]octane];
(R)-8-methyl-3H-1'-azaspiro[benzo[4,5]imidazo[2,1-b]oxazole-2,3'-bicyclo[2.2.2]octane];
(S)-8-methyl-3H-1'-azaspiro[benzo[4,5]imidazo[2,1-b]oxazole-2,3'-bicyclo[2.2.2]octane];
(R)-8-(trifluoromethyl)-3H-1'-azaspiro[benzo[4,5]imidazo[2,1-b]oxazole-2,3'-bicyclo[2.2.2]octane];
(S)-8-(trifluoromethyl)-3H-1'-azaspiro[benzo[4,5]imidazo[2,1-b]oxazole-2,3'-bicyclo[2.2.2]octane];
(R)-8-(4-methoxyphenyl))-3H-1'-azaspiro[benzo[4,5]imidazo[2,1-b]oxazole-2,3'-bicyclo[2.2.2]octane];
(S)-8-(4-methoxyphenyl))-3H-1'-azaspiro[benzo[4,5]imidazo[2,1-b]oxazole-2,3'-bicyclo[2.2.2]octane];
(R)-7-(pyridin-3-yl)-3H-1'-azaspiro[benzo[4,5]imidazo[2,1-b]oxazole-2,3'-bicyclo[2.2.2]octane];
(S)-7-(pyridin-3-yl)-3H-1'-azaspiro[benzo[4,5]imidazo[2,1-b]oxazole-2,3'-bicyclo[2.2.2]octane];
(R)-2-phenyl-6H-1'-azaspiro[oxazolo[3,2-b][1,2,4]triazole-5,3'-bicyclo[2.2.2]octane];
(S)-2-phenyl-6H-1'-azaspiro[oxazolo[3,2-b][1,2,4]triazole-5,3'-bicyclo[2.2.2]octane];
2-bromo-6H-1'-azaspiro[oxazolo[3,2-b][1,2,4]triazole-5,3'-bicyclo[2.2.2]octane];
2-chloro-6H-1'-azaspiro[oxazolo[3,2-b][1,2,4]triazole-5,3'-bicyclo[2.2.2]octane];
6H-1'-azaspiro[oxazolo[3,2-b][1,2,4]triazole-5,3'-bicyclo[2.2.2]octane];
7-bromo-6-methyl-3H-1'-azaspiro[oxazolo[2',3':2,3]imidazo[4,5-b]pyridine-2,3'-bicyclo[2.2.2]octane];
7-bromo-3H-1'-azaspiro[oxazolo[2',3':2,3]imidazo[4,5-b]pyridine-2,3'-bicyclo[2.2.2]octane];
7-chloro-3H-1'-azaspiro[oxazolo[2',3':2,3]imidazo[4,5-b]pyridine-2,3'-bicyclo[2.2.2]octane];
(R)-6-phenyl-3H-1'-azaspiro[imidazo[2,1-b]oxazole-2,3'-bicyclo[2.2.2]octane]; and
(S)-6-phenyl-3H-1'-azaspiro[imidazo[2,1-b]oxazole-2,3'-bicyclo[2.2.2]octane]
or a pharmaceutically acceptable salt or stereoisomer thereof.

12. A compound according to claim 1 which is
(R)-7-Methoxy-3H-1'-azaspiro[benzo[4,5]imidazo[2,1-b]oxazole-2,3'-bicyclo[2.2.2]octane];
(R)-7-methyl-3H-1'-azaspiro[benzo[4,5]imidazo[2,1-b]oxazole-2,3'-bicyclo[2.2.2]octane];
R)-7-(trifluoromethyl)-3H-1'-azaspiro[benzo[4,5]imidazo[2,1-b]oxazole-2,3'-bicyclo[2.2.2]octane];
(R)-8-methyl-3H-1'-azaspiro[benzo[4,5]imidazo[2,1-b]oxazole-2,3'-bicyclo[2.2.2]octane];
(R)-2-phenyl-6H-1'-azaspiro[oxazolo[3,2-b][1,2,4]triazole-5,3'-bicyclo[2.2.2]octane];
(S)-6-phenyl-3H-1'-azaspiro[imidazo[2,1-b]oxazole-2,3'-bicyclo[2.2.2]octane];
or a pharmaceutically acceptable salt or stereoisomer thereof.

13. A pharmaceutical composition comprising a therapeutically effective amount of a compound of claim 1, or a pharmaceutically acceptable salt thereof, and a pharmaceutically acceptable carrier.

\* \* \* \* \*